US009351701B2

(12) United States Patent
Yamakawa et al.

(10) Patent No.: US 9,351,701 B2
(45) Date of Patent: May 31, 2016

(54) APPARATUS FOR CALIBRATING PHOTON-COUNTING TYPE OF RADIATION DETECTOR AND METHOD OF CALIBRATING THE SAME

(75) Inventors: Tsutomu Yamakawa, Osaka (JP); Daisuke Hashimoto, Osaka (JP); Hideyuki Nagaoka, Osaka (JP); Tatsuya Nagano, Osaka (JP); Masahiro Tsujita, Osaka (JP)

(73) Assignee: TAKARA TELESYSTEMS CORP., Osaka-Shi, Osaka (JP)

( * ) Notice: Subject to any disclaimer, the term of this patent is extended or adjusted under 35 U.S.C. 154(b) by 146 days.

(21) Appl. No.: 14/111,945

(22) PCT Filed: Apr. 20, 2012

(86) PCT No.: PCT/JP2012/060692
§ 371 (c)(1),
(2), (4) Date: Dec. 31, 2013

(87) PCT Pub. No.: WO2012/144589
PCT Pub. Date: Oct. 26, 2012

(65) Prior Publication Data
US 2014/0105370 A1  Apr. 17, 2014

(30) Foreign Application Priority Data

Apr. 21, 2011  (JP) .................................. 2011-094953

(51) Int. Cl.
*G01D 18/00* (2006.01)
*A61B 6/00* (2006.01)
(Continued)

(52) U.S. Cl.
CPC ................. *A61B 6/585* (2013.01); *A61B 6/025* (2013.01); *A61B 6/032* (2013.01); *A61B 6/14* (2013.01);
(Continued)

(58) Field of Classification Search
CPC .... A61B 6/585; A61B 6/4233; A61B 6/4241; G01D 18/00
USPC ............................... 378/98.8, 207; 250/252.1
See application file for complete search history.

(56) References Cited

U.S. PATENT DOCUMENTS

2004/0200969 A1  10/2004 Odogba et al.
2008/0192899 A1   8/2008 Kump et al.
2010/0296627 A1  11/2010 Inoue et al.

FOREIGN PATENT DOCUMENTS

CN  101889869 A  11/2010
JP  S58-076789 A   5/1983
(Continued)

OTHER PUBLICATIONS

International Preliminary Report on Patentability with its English Translation, issued Oct. 22, 2013, incorporating the English translation of the Written Opinion of the ISA, mailed Jul. 24, 2012.
(Continued)

*Primary Examiner* — Jurie Yun
(74) *Attorney, Agent, or Firm* — Harness, Dickey & Pierce, P.L.C.

(57) ABSTRACT

There is provided a calibration apparatus used for a photon counting type of radiation detector. In this apparatus, a radiation condition of a radiation is set such that particles of the radiation (X-rays) which are incident on a plurality of detection modules are piled up over each other at a probability which is equal to or less than a predetermined value. Under the setting of this radiation condition, detection sensitivities for the radiation are made uniform among the plurality of detection modules. Using this uniformed result, the detection sensitivities for the radiation are further made uniform every channel of each of the pixels formed by circuit groups including the plurality of detection modules, discrimination circuits and data calculation circuits and every discrimination circuit in each channel.

20 Claims, 17 Drawing Sheets

(51) Int. Cl.
*A61B 6/02* (2006.01)
*A61B 6/03* (2006.01)
*A61B 6/14* (2006.01)
*G01T 1/17* (2006.01)
*G01T 1/24* (2006.01)

(52) U.S. Cl.
CPC ............ *A61B 6/4233* (2013.01); *A61B 6/4241* (2013.01); *A61B 6/482* (2013.01); *G01T 1/171* (2013.01); *G01T 1/243* (2013.01)

(56) References Cited

FOREIGN PATENT DOCUMENTS

| | | |
|---|---|---|
| JP | H08-304551 A | 11/1996 |
| JP | 11-109040 A | 4/1999 |
| JP | 2006-101926 A | 4/2006 |

OTHER PUBLICATIONS

Extended European search report dated Feb. 27, 2015 in corresponding European Application No. 12774007.4.
Schlomka, J.P., et al., "Experimental feasibility of multi-energy photon-counting K-edge imaging in pre-clinical computed tomography," Physics in Medicine and Biology, vol. 53, No. 15, pp. 4031-4047, Jul. 8, 2008.
Bergamaschi, A., et al., "Photon counting microstrip detector for time resolved powder diffraction experiments," Nuclear Instruments & Methods in Physics Research A, vol. 604, No. 1-2, pp. 136-139, Jun. 1, 2009.
De Ruijter, W. J., "Imaging Properties and Applications of Slow-Scan Charge-Coupled Device Cameras Suitable for Electron Microscopy," Micron, vol. 26, No. 3, pp. 247-275, 1995.
J.S. Iwanczyk, et al, "Photon Counting Energy Dispersive Detector Arrays for X-ray Imaging"; Nuclear Science Symposium Conference Record, 2007.; NSS' 07, IEEE.
International Search Report for PCT/JP2012/060692, ISA/JP, mailed Jul. 24, 2012.

FIG.19

| ACQUISITION CHANNEL Cn | | CALIBRATION DATA |
|---|---|---|
| ACQUISITION PIXEL Sn | DISCRIMINATION CIRCUIT DSi | |
| 1 | 1 | $TH_{AVE} + \Delta th1$ |
| | 2 | $TH_{AVE} + \Delta th2$ |
| | 3 | $TH_{AVE} - \Delta th3$ |
| | 4 | $TH_{AVE} - \Delta th4$ |
| 2 | 1 | $TH_{AVE} - \Delta th5$ |
| | 2 | $TH_{AVE} + \Delta th6$ |
| ⋮ | ⋮ | ⋮ |
| N | 3 | ⋮ |
| | 4 | ⋮ |

$n = 1 \sim N$
$i = 1 \sim 4$

APPARATUS FOR CALIBRATING PHOTON-COUNTING TYPE OF RADIATION DETECTOR AND METHOD OF CALIBRATING THE SAME

CROSS-REFERENCE TO RELATED APPLICATIONS

This application is a 371 U.S. National Stage of International Application No. PCT/JP2012/060692, filed Apr. 20, 2012, Year. This application claims priority to Japanese Patent Application No. 2011-094953, filed Apr. 21, 2011. The disclosures of the above applications are incorporated herein by reference.

TECHNICAL FIELD

The present invention relates to a calibration device for a radiation detector and a calibration method therefor and in particular to a calibration device for a photon counting type of radiation detector and a calibration method therefor.

TECHNICAL BACKGROUND

In recent years, remarkable technical development can be seen in those devices which diagnose/image the inner structure or function of an object by means of radiation, such as X-ray beams and gamma-ray beams. For this type of devices, detectors for detecting radiation are essential. Enhancement of performance of such radiation detectors also contributes to the above technical development. In particular, enhancement of performance is promoted in so-called digitization, with which a detection signal is outputted in digital form, as well as achievement of fine pixels and enlargement of a sensor surface.

As a detection method of such a radiation detector, a detection method called the photon counting method attracts attention, in addition to the conventionally used integration method (integration mode). The photon counting method has been applied to a gamma-ray detector in the field of nuclear medicine (e.g., see Patent Document 1: JP-A-H11-109040). On the other hand, according to some reported cases of recent years, the photon counting method is applied to an X-ray detector in order to achieve the effect of improving the image enhancement ability, reducing the metal artifacts, mitigating the impact of beam hardening, and the like.

As one of such application cases, the one suggested in Patent Document 2: JP-A-2006-101926 is well known. Specifically, the document suggests: "A radiation detection apparatus including a photon counting type detector that deals with radiation as photons, the radiation being incident on each of a plurality of acquisition pixels, to output an electrical signal according to the energy of the particles, wherein: based on the signal outputted by the detector for each acquisition pixel, the apparatus calculates a count data of the number of particles of the radiation, which are classified into a plurality of energy ranges in an energy spectrum of radiation; the apparatus performs weighting with respect to the count data of each of the plurality of energy ranges of each acquisition pixel subjected to the calculation, using a weight coefficient given to each of the energy ranges; the apparatus adds the count data of the respective plurality of energy ranges of each weighted acquisition pixel; and the apparatus outputs the addition data as radiation image generation data for each acquisition pixel".

Thus, in a photon counting type X-ray detector, one or more thresholds (preferably, a plurality of thresholds) are prepared to discriminate the energy which is possessed by each incident X-ray photon. Since the range of energy is defined by the thresholds, the energy range to which the energy of each X-ray photon belongs can be determined. As a result of the determination, measurement is performed for the number of X-ray photons discriminated into the respective energy ranges. The information of the measured number is reflected to a pixel value of an image.

In the photon counting type X-ray detector, upon entry of X-ray photons into pixels (i.e. acquisition pixels), an electric pulse signal is outputted from each acquisition pixel. The energy of the X-ray photons incident on each pixel is reflected to a peak value of the pulse signal generated by the X-ray photons. The value of data outputted from each acquisition pixel depends on which of the thresholds the peak value exceeds. Therefore, each threshold is required to be retained with high accuracy with respect to the energy possessed by the X-ray photons and with as much evenness as possible between the acquisition pixels. The accuracy and the evenness are influenced by the sensitivity of each X-ray sensing element configuring an acquisition pixel, and by the difference in the characteristics of a circuit formed of a CMOS on an output channel side of each element. Therefore, it has been necessary to calibrate each acquisition pixel and each threshold of the pixel to adjust the sensitivity of each acquisition pixel with respect to the energy of X-ray photons so that the sensitivity will be the same or is considered to be the same between the acquisition pixels.

Conventionally, this calibration has been performed using a plurality of gamma-ray sealed radiation sources, such as 241-Am (59.5 keV) or 57-Co (122 keV) having a known energy value. Specifically, the radiation sources are placed in front of a sensor surface of an X-ray detector and gamma-ray beams are radiated for a predetermined period. The X-ray sensing element that has received radiation of the gamma-ray beams outputs an electric pulse in accordance with the known energy value. Using the signal value from each acquisition pixel, the thresholds given to each acquisition pixel are adjusted so that the sensitivity (generally called S-characteristics in which the output is distorted in lower intensities and higher intensities in the signal: amplitude of electric pulse relative to energy value is indicated) with respect to the energy value of X-ray photons will be substantially the same between the acquisition pixels, i.e. between acquisition channels.

An example of setting thresholds described in Non-patent Document 1 is also well known. In the example described in this document, one threshold is ensured to be given to a detector that uses CdTe.

PRIOR ART DOCUMENTS

Patent Documents

Patent Document 1: JP-A-H11-109040
Patent Document 2: JP-A-2006-101926

Non-Patent Documents

Non-patent Document 1: J. S. Iwanczyk, et al, "Photon Counting Energy Dispersive Detector Arrays for X-ray Imaging"; Nuclear Science Symposium Conference Record, 2007.; NSS '07, IEEE

SUMMARY OF THE INVENTION

Problems to be Solved by the Invention

However, the foregoing calibration method using gamma-ray sealed radiation sources has suffered from the following problems when applied to an X-ray detector of recent years, in which pixel size is very small (e.g., 200 μm×200 μm).

In the first place, since the size of each pixel (acquisition pixel) of the X-ray detector is small, the number of X-ray (γ-ray) photons incident on each acquisition pixel is small. Specifically, since the rate of radiation is extremely low, when the acquisition pixels are attempted to be all calibrated, it takes an extremely long time, e.g. hours, for the acquisition. For this reason, a great deal of time and labor has to be spent for the work of preparation and this imposes a burden on an operator. As a result, the operating rate of the diagnostic apparatus is lowered. Further, the amount of radiation used for calibration differs vastly from the actually used amount of radiation. This raises a problem that the accuracy of calibration is not enhanced.

Further, since each gamma-ray source has discrete energy, retaining the accuracy of thresholds has been very difficult because of the gain and offset, or the S-shaped non-linear input/output characteristics, or the like, of each pre-amplifier circuit. When a pixel is as small as not more than 200 μm, positive effects obtained from the smallness are great. However, it is very difficult to retain the hardware accuracy in realizing the positive effects.

On the other hand, measurement may be performed by using unsealed radiation sources and enhancing the intensity of gamma-ray beams. However, this is not practical because these sources are difficult to handle.

The detector described in the foregoing Non-patent Document 1 has a single threshold and each acquisition pixel has a large size which is 1 mm×1 mm. When a single threshold is used, it is only required to count the number of all incident X-ray particles, similar to an integral type detector. Accordingly, the accuracy of calibration is not so problematic but may be manageable by correcting evenness after acquiring X-ray transmission data. In contrast, in the case where each acquisition pixel is small and a plurality of thresholds are set with respect to each acquisition pixel, it is quite important, as mentioned above, to perform calibration with high accuracy.

The present invention has been made in light of the conditions set forth above and has as its object to provide a calibration method for a photon counting type radiation detector which is able to perform calibration for each acquisition pixel with high accuracy and in a short time.

Means for Solving the Problems

In order to achieve the above object, the present invention provides as one mode a calibration apparatus used in a photon counting type of radiation detector, the radiation detector comprising: a detector provided with a plurality of modules, each of the modules having a plurality of detection elements provided as a plurality of pixels, each of the elements detecting, as a photon, a radiation radiated from a radiation source and outputting an electric pulse signal whose quantity depends on energy of the photon; at least one discrimination circuit provided for discriminating amounts of the energy in an energy spectrum of the radiation, wherein at least one energy threshold for setting a plurality of energy ranges are provided to each of the pixels; a data production circuit producing counting data indicative of the number of particles of the radiation every pixel and every energy range, based on a count of the pulse signal outputted from each of the plurality of detection elements; and image production means for producing an image of an object based on the count data produced by the data production circuit, when the radiation is radiated to the object. The apparatus comprises radiation condition setting means for setting a radiation condition of the radiation such that, when the particles of the radiations are incident on the plurality of detection modules, a probability of pileups of the incident particles is smaller than or equal to a predetermined value; first calibrating means for calibrating the detection modules such that, in a state where the radiation condition is set for the radiation by the radiation condition setting means, detection sensitivities for the radiation are uniformed among the plurality of detection modules or at the respective detection modules; and second calibrating means for calibrating the modules, based on results calibrated by the first calibration circuit, such that the detection sensitivities for the radiation are uniformed every channel and every discrimination circuit in each channel provided in a circuit group including, at least, the plurality of detection modules, the discrimination circuit, and the data production circuit.

Advantageous Effects of the Invention

According to the present invention, detection sensitivity is uniformed first between the plurality of detection modules or for each detection module. After that, the detection sensitivity is uniformed for each channel at each of the pixels, and for each discrimination circuit in each channel, i.e. for each energy threshold. Thus, the present invention can provide a calibration method for a photon counting type radiation detector, the method being able to perform highly accurate calibration in a short time for a plurality of detection modules and each acquisition pixel thereof, using one type of radiation source, such as an X-ray source.

BRIEF DESCRIPTION OF THE DRAWINGS

FIG. 19 is a table illustrating how calibration data are set;

MODES FOR IMPLEMENTING THE PRESENT INVENTION

With reference to the accompanying drawings, hereinafter are described some embodiments of the present invention.

First Embodiment

Referring to FIGS. 1 to 20, hereinafter is described a preferred embodiment of a calibration device for a photon counting type radiation detector and a calibration method therefor, related to a first embodiment of the present invention. The photon counting type radiation detector is implemented, as an example, as a photon counting type X-ray detector (hereinafter referred to as X-ray detector). The X-ray detector is applied to a medical X-ray CT (computed tomography) scanner or an X-ray panoramic imaging apparatus. In the following description of the present embodiment, an example of an X-ray panoramic imaging apparatus (hereinafter referred to as panoramic imaging apparatus) is used.

Figure 1:
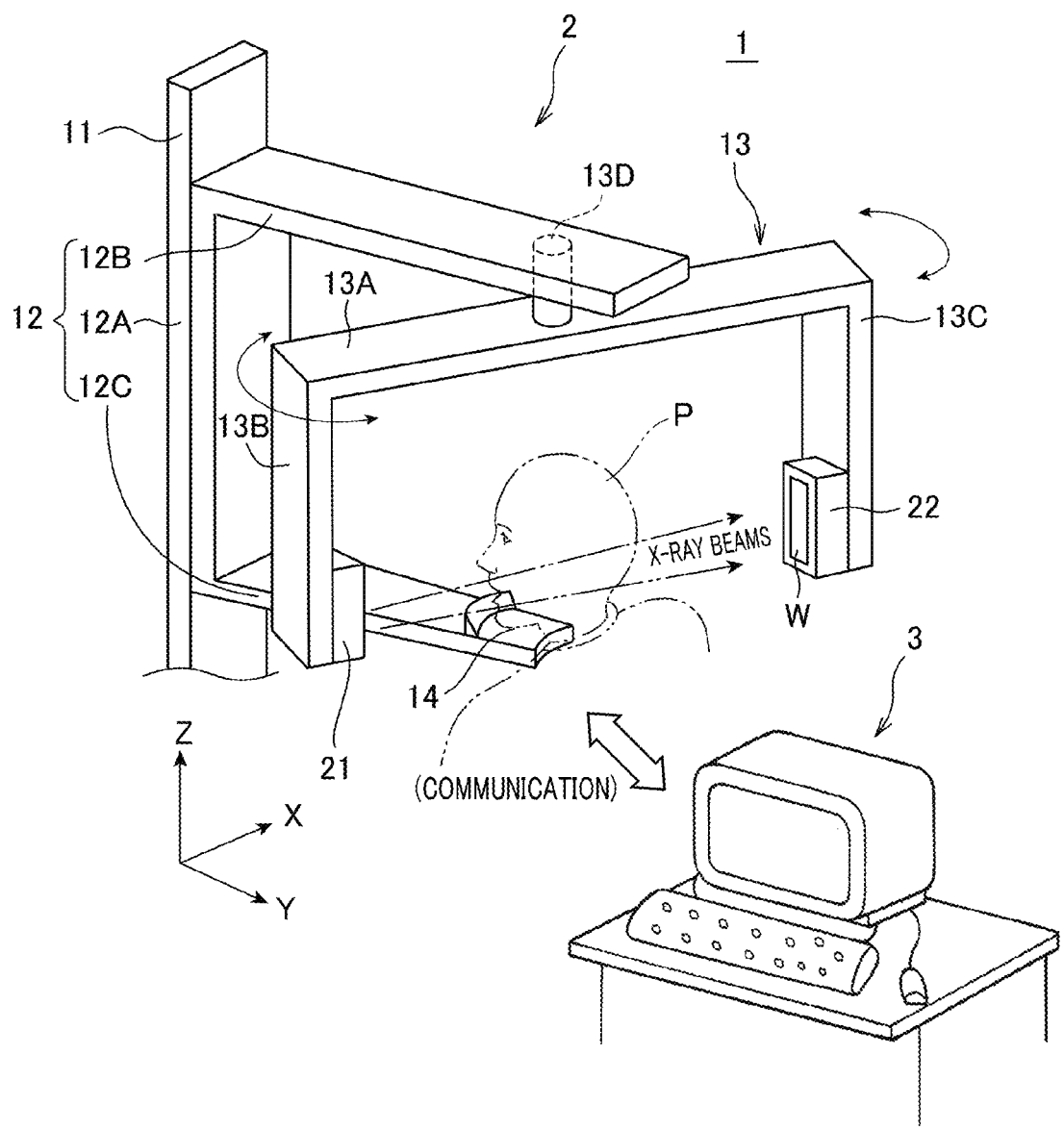
FIG. 1 is a partial perspective view schematically illustrating the appearance of a dental panoramic imaging apparatus as a radiation imaging apparatus related to a first embodiment of the present invention.

FIG. 1 schematically illustrates a panoramic imaging apparatus 1. The panoramic imaging apparatus 1 includes a gantry (data acquisition device) 2 that acquires data from an object being examined P, and a console 3 that processes the acquired data to prepare an image or the like and controls the operation of the gantry 2.

The gantry 2 includes a support pillar 11. A longitudinal direction in which the support pillar extends is referred to as vertical direction (or up-and-down direction: Z-axis direction), and a direction perpendicular to the vertical direction is referred to as a horizontal direction (direction along an X-Y plane). The support pillar 11 includes a U-shaped vertical-movement arm unit 12 which is movable in the vertical direction. The vertical-movement arm unit 12 includes a vertical arm 12A that is movable along the support pillar 11, an upper-side horizontal arm 12B and a lower-side horizontal arm 12C which extend in the horizontal direction from upper and lower ends, respectively, of the vertical arm 12A. A pivotal arm unit 13 is mounted to the upper-side horizontal arm 12B at its predetermined position, in a state of being pivotally movable in a horizontal plane perpendicular to the support pillar 11. The lower-side arm 12C has an end portion configured as a chin rest 14 on which the chin of the object being examined P is placed. Thus, in imaging, the object being examined P is imaged, as indicated by a phantom line in the figure, with his/her chin being placed on the chin rest. The vertical position of the vertical-movement arm unit 12 is adjusted according to the height of the object being examined P by a drive mechanism, not shown.

The pivotal arm unit 13 includes a horizontal arm 13A substantially having a shape of upside down U, and a radiation-source-side vertical arm 13B and a detection-side vertical arm 13C which extend downward from both ends of the horizontal arm 13A. The horizontal arm 13A is hung down by a rotary shaft 13D and pivotally moved (rotated) about the rotary shaft 13D by a drive mechanism, such as an electric motor, not shown. The radiation-source-side arm 13B has a lower end portion which is provided with an X-ray tube 21. An X-ray beam radiated as a pulse X-ray beam, for example, from the X-ray tube 21 is collimated by a collimator (not shown) which is also provided at the lower end portion. The collimated X-ray beam is then transmitted through the chin portion of the object being examined P and propagates to the detection-side vertical arm 13C (see the phantom line). The detection-side vertical arm 13C has a lower end portion which is provided with an X-ray detector 22 (hereinafter referred to as detector) having an X-ray incident window W (e.g., 5.0 mm wide×145 mm high). The detector 22 has a sensor surface having a size, for example, of 6.4 mm wide×150 mm high).

Figure 2:
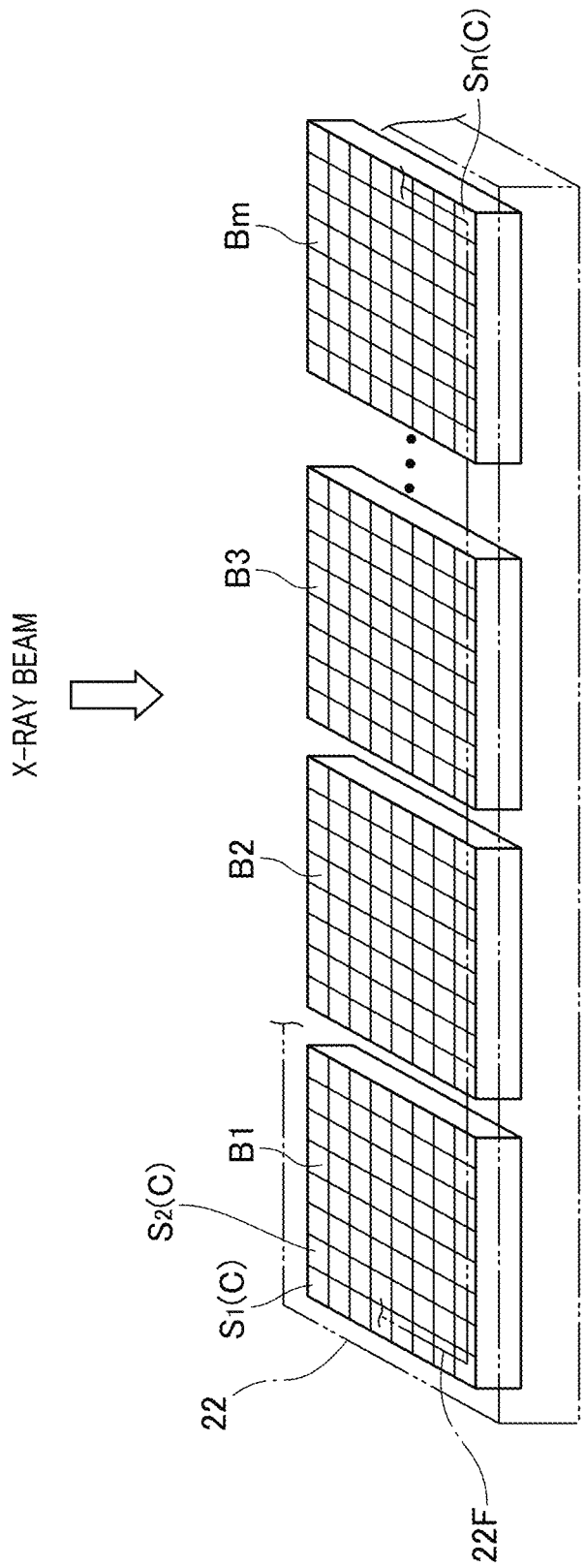
FIG. 2 is a perspective view schematically illustrating a detector that uses a plurality of detection modules.

As shown in FIG. 2, the detector 22 has a plurality of detection modules B1 to Bn in which X-ray imaging elements are two-dimensionally arrayed. The plurality of detection modules B1 to Bn as a whole configure a detection part. The plurality of modules B1 to Bm are formed as blocks independent of each other and mounted on a substrate (not shown), with each block being in a predetermined shape (e.g., rectangular shape), thereby forming the whole detector 22. Each detection module B1 (to Bm) is made of a semiconductor material that directly converts X-ray beams to electric pulse signals. Thus, the detector 22 is a photon counting type X-ray detector based on a direct conversion method using semiconductors.

As mentioned above, the detector 22 is formed as an assembly of the plurality of detection modules B1 to Bm. The detector 22 has acquisition pixels Sn (n=1 to N: the number of pixels N equals, for example, to 50×1450 pixels) which are two-dimensionally arranged in the entirety (see FIG. 2). For example, the size of each acquisition pixel Sn is 200 μm×200 μm.

Thus, the detector 22 counts photons corresponding to incident X-ray beams for each pixel (acquisition pixel) Sn (n=1 to N) configuring the sensor surface of the detector. The detector 22 then outputs electric data reflecting the count at a high frame rate of 300 fps or the like. This data is also called frame data.

Each of the plurality of acquisition pixels Sn is configured by a scintillator, such as a cadmium telluride semiconductor (CdTe semiconductor), a cadmium zinc telluride semiconductor (CdZnTe semiconductor), a silicon semiconductor (Si semiconductor) or cesium iodile (CsI), and a photoelectric converter configured by a semiconductor cell (sensor) C, such as a C-MOS. Each of the semiconductor cells C detects incident X-ray beams and outputs a pulsed electric signal according to the energy value. Specifically, the detector 22 includes a group of cells in which a plurality of semiconductor cells C are two-dimensionally arrayed. Further, each of the semiconductor cells C, i.e. each of the two-dimensionally arrayed plurality of acquisition pixels Sn, has an output side provided with a data acquisition circuit $51n$ (n=1 to N). A path extending from each of the acquisition pixels Sn, i.e. each of the semiconductor cells C, to each data acquisition circuit $51_1$ (to $51_N$) is referred to as an acquisition channel CNn (n=1 to N), as necessary.

The structure of the group of semiconductor cells S is also well known as disclosed by JP-A-2000-069369, JP-A-2004-325183 and JP-A-2006-101926.

The size (200 µm×200 µm) of each acquisition pixel Sn mentioned above is set to a sufficiently small value that enables detection of X-ray beams as photons (particles). In the present embodiment, the size that enables detection of X-ray beams as the particles is defined to be "the size that can virtually ignore the occurrence of superimposition phenomenon (also called pileup) between electric pulse signals responding to a plurality of successive incidences of radiation (e.g., X-ray) particles on the same position or the vicinity thereof, or the size that can predict the amount of the successive incidences". The occurrence of the superimposition phenomenon causes count loss (also called pileup count) of X-ray particles in the characteristics of "the number of incidences to actual count" of the X-ray particles. Therefore, the size of each of the acquisition pixels formed in the X-ray detector 12 is set to the size that would not cause or substantially does not cause count loss, or to a level that enables estimation of the amount of the count loss.

Figure 3:
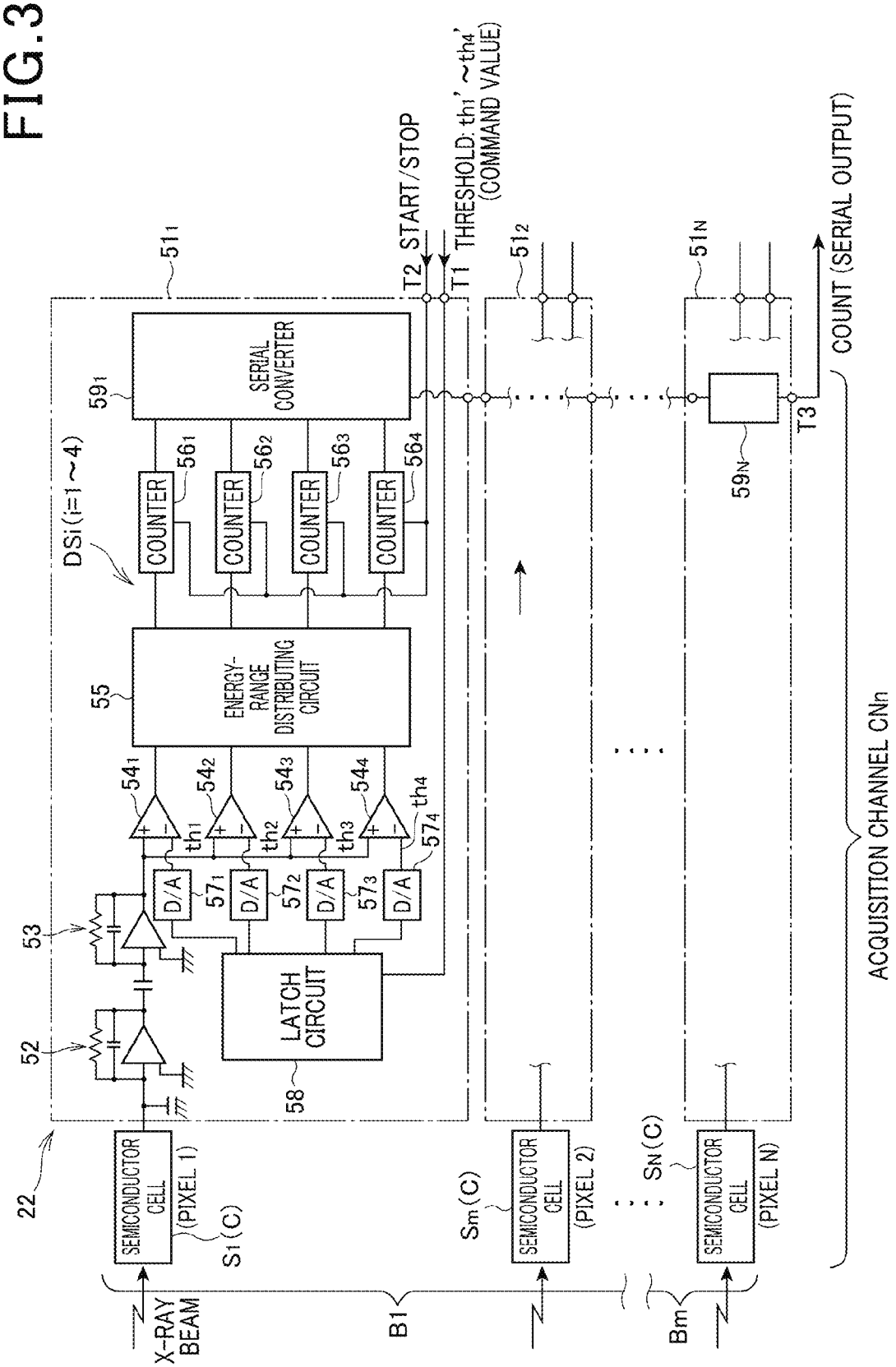
FIG. 3 is a block diagram schematically illustrating an electrical configuration of a photon counting type X-ray detector installed in the panoramic imaging apparatus.

Referring now to FIG. 3, hereinafter is described a circuit electrically connected to the detector 22. Each of the plurality of data acquisition circuits $51n$ (n=1 to N) has a charge amplifier 52 that receives an analog electric signal outputted from each semiconductor cell C. Downstream of the charge amplifier 52, the data acquisition circuit $51n$ includes a waveform shaping circuit 53, a multiple-stage comparator $52_1$ to $54_i$ (here i=4), an energy-range distribution circuit 55, multiple-stage counters $56_1$ to $56_i$ (here i=4), multiple-stage D/A converters $57_1$ to $57_i$ (here i=4), latch circuit 58 and a serial converter 59.

Each charge amplifier 52 is connected to each current-collecting electrode of each semiconductor cell S, charges up charges collected in response to the incidence of X-ray particles and outputs the charges as an electric pulse signal. The charge amplifier 52 has an output terminal connected to the waveform shaping circuit 53 whose gain and offset are adjustable. The waveform shaping circuit 53 shapes the waveform of a detected pulse signal by processing it with the gain and offset that have been adjusted in advance. The gain and offset of the waveform shaping circuit 53 are calibrated, taking account of unevenness with respect to charge characteristics and variation in the characteristics of each circuit, for each acquisition pixel Sn configured by the semiconductor cell C. This can enhance the output of a waveform shaping signal removed with unevenness and enhance the accuracy of setting a relative threshold thereto. As a result, a waveform-shaped pulse signal corresponding to each acquisition pixel Sn, i.e. outputted from the waveform shaping circuit 53 of each acquisition channel CNn, will substantially have characteristics reflecting the energy value of the incident X-ray particles. Accordingly, the variation between the acquisition channels CNn is remarkably improved.

Figure 4:
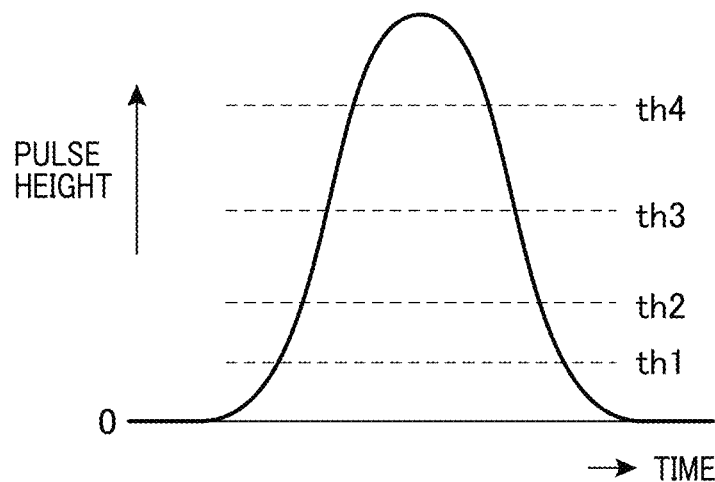
FIG. 4 is a diagram illustrating a relationship between peak value (energy) of an electric pulse as a detection signal generated by X-ray photons, and thresholds set for discriminating energy in the detector.

The waveform shaping circuit 53 has an output terminal connected to the comparison input terminals of the plurality of comparators $54_1$ to $54_4$. As shown in FIG. 4, the plurality of comparators $54_1$ to $54_4$ have respective reference input terminals to which respective analog thresholds $th_i$ (here i=1 to 4) having a different value are applied. Thus, a single pulse signal can be separately compared with the different analog thresholds $th_1$ to $th_4$. The reason for the comparison is to check which of the energy ranges set in advance by being divided into a plurality of divisions the energy value of the incident X-ray particles belongs (is discriminated) to. The peak value (that shows the energy value of the incident X-ray particles) of the pulse signal is determined as to which of the values of the analog thresholds $th_1$ to $th_4$ it exceeds. The energy range to which the peak value is discriminated depends on this determination. Normally, the smallest analog threshold $th_1$ is set as a threshold that ensures not to detect disturbance, or noises caused by circuits, such as the semiconductor cell S and the charge amplifier 42, or low-energy radiation unnecessary for imaging. The number of thresholds, i.e. the number of comparators, is not necessarily limited to four but may be any number, e.g. one including the analog threshold $th_1$, or two or more.

Specifically, the analog thresholds $th_1$ to $th_4$ are provided, in digital values, to each acquisition pixel Sn, i.e. each acquisition channel, from a calibration calculator 38 of the console 3 via an interface 32. Accordingly, the reference input terminals of the respective comparators $54_1$ to $54_4$ are connected to the output terminals of the four D/A converters $57_1$ to $57_4$, respectively. The D/A converters $57_1$ to $57_4$ are connected to a threshold reception terminal $T_1$ (to $T_N$) via the latch circuit 58. The threshold reception terminal $T_1$ (to $T_N$) is connected to the interface 32 of the console 3.

In imaging, the latch circuit 58 latches digital thresholds $th_1'$ to $th_4'$ provided from a threshold providing unit 40 via an interface 31 and the threshold reception terminal $T_1$ (to $T_N$) and outputs the latched thresholds $th_1'$ to $th_4'$ to the D/A converters $57_1$ to $57_4$, respectively. Thus, the D/A converters $57_1$ to $57_4$ are able to provide the instructed analog thresholds $th_1$ to $th_4$, as voltage, to the comparators $54_1$ to $54_4$, respectively. Each acquisition channel CNn is connected to one or more circuit systems which extend from the D/A converter $57_i$ (i=1 to 4) to the counter $55_i$ (i=1 to 4) via the comparator $54_i$ (i=1 to 4). This circuit system is referred to as "discrimination circuit" $DS_i$ (i=1 to 4).

Figure 5:
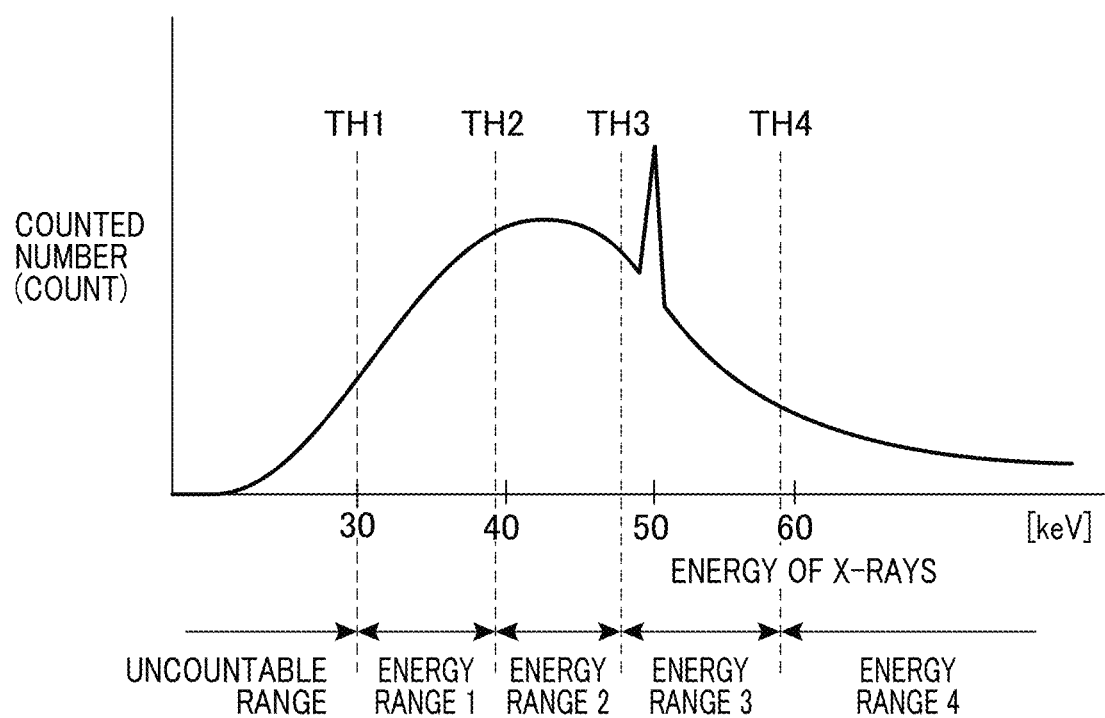
FIG. 5 is a diagram illustrating a relationship between X-ray energy, energy ranges to be discriminated and counted number of photons.

FIG. 5 shows an example of setting an energy threshold $TH_i$ (i=1 to 4) equivalent to the analog threshold $th_i$ (i=1 to 4). As a matter of course, the energy threshold $TH_i$ is a discrimination value which is discretely set and can be optionally set by a user.

The analog threshold $th_i$ is an analog voltage provided to the comparator $54_i$ in each discrimination circuit $DS_i$, and the energy threshold $TH_i$ is an analog value for discriminating the X-ray energy (keV) of an energy spectrum. The waveform in FIG. 5 shows a continuous spectrum of the X-ray energy radiated from a normally used X-ray tube. The counted value (count) indicated by the vertical axis is in proportion to the photon occurrence frequency that corresponds to the energy value indicated by the horizontal axis. The energy value of the horizontal axis relies on the tube voltage of the X-ray tube 21. With respect to this spectrum, the first analog threshold $th_1$ is set correspondingly with the energy threshold $TH_1$ that can discriminate an uncountable range of the number of X-ray particles from a low-energy range 1. The second, third and fourth analog thresholds $th_2$, $th_3$ and $th_4$ are set so as to sequentially provide the second, third and fourth energy thresholds $TH_2$, $TH_3$ and $TH_4$, each having a higher value than the first energy threshold $TH_1$. Thus, appropriate discrimination points are defined on the basis of the characteristics of the energy spectrum waveform and design values and hence energy ranges 2 to 4 are set.

Assuming one or more reference objects being examined, the energy threshold $TH_i$ is determined so that the count in a predetermined period of each energy range will be substantially constant.

Accordingly, as shown in FIG. 3, the output terminals of the comparators $54_1$ to $54_4$ are connected to the energy-range distribution circuit 55. The energy-range distribution circuit 55 interprets the outputs of the plurality of comparators $54_1$ to $54_4$, that is, interprets results of comparison between a pulse voltage corresponding to the energy value of the detected X-ray particles and the analog threshold $th_1$ (to $th_4$), and performs distribution, taking account of which of the energy ranges 1 to 4 the energy value is to be classified. For example, when the outputs of two comparators $54_1$ and $54_2$ are in an on-state (detection value≥threshold) and the outputs of the remaining two comparators $54_3$ and $54_4$ are in an off-state (detection value<threshold), the energy value is discriminated to the energy range 2. Also, when the outputs of three comparators $54_1$ to $54_3$ are in an on-state and the output of the remaining comparator $54_4$ is in an off-state, the energy value is discriminated to the energy range 3. The same applies to other events. The energy-range distribution circuit 55 transmits a pulse signal according the results of discrimination to any one of the counters $56_1$ to $56_4$. For example, when there is an event discriminated to the energy range 1, a pulse signal is transmitted to the first-stage counter $56_1$. When there is an event discriminated to the energy range 2, a pulse signal is transmitted to the second-stage counter $56_2$. The same applies to the energy ranges 3 and 4.

Each of the counters $56_1$ to $56_4$ counts up a pulse signal every time it is inputted from the energy-range distribution circuit 55. Thus, each of the counters $56_1$ to $56_4$ is able to measure the number of X-ray particles of the energy value discriminated to the corresponding energy range, as an integrated value of each predetermined period. The counters $56_1$ to $56_4$ are provided with start and stop signals from a controller 33 of the console 3 via a start/stop terminal T2. The measurement of the predetermined period is externally managed using a reset circuit possessed by each counter.

In this way, the number of particles of the X rays incident on the detector 12 is measured for each acquisition pixel Sn and for each energy range by the plurality of counters $56_1$ to $56_4$ in the predetermined period before the measurement is reset. The counts of the X-ray particles are parallelly outputted from the counters $56_1$ to $56_4$ as digital count data and then converted to a serial format by the serial converter 59. The serial converter $59_1$ is connected in series with the serial converters $59_2$ to $59_N$ of all of the remaining acquisition channels. Accordingly, all digital count data are outputted from the serial converter $59_N$ of the last channel and transmitted to the console 3 via a transmission terminal T3. In the console 3, the interface 31 receives the count data for storage in a first storage 34.

Then, an image processor 35 reads the count data stored in the first storage 34 in accordance with an instruction of an operator received from an input device 37. Then, using the count data, the image processor 35 reconfigures an X-ray transmission image (panoramic image) of a cross section along a tooth row, for example, on the basis such as of a tonnosynthesis method. The count data of the plurality of energy ranges 1 to 4 are obtained from each acquisition pixel Sn. Accordingly, for example, in reconfiguring the panoramic image, the image processor 35 performs weighting with more weight for the count data having higher energy value, followed by addition of the results. Thus, acquired data are prepared for each acquisition pixel Sn. In this way, the data acquired from all the acquisition pixels Sn accompanying the X-ray scan get together. These acquired data are processed using the tonnosynthesis method to reconfigure a panoramic image. For example, the panoramic image is displayed by a display 36. As a matter of course, a panoramic image may be reconfigured without performing weighting.

There are a variety of methods for performing weighting. As mentioned above, when a weighting process is performed such that the count data of a higher-energy range are emphasized, the artifacts due to beam hardening can be suppressed. Alternatively, weighting may be performed such that a lower-energy range is emphasized for the purpose of improving the contrast of soft tissue. Alternatively, both of the ranges may be emphasized in weighting, for the purpose of suppressing artifacts due to hardening and improving the contrast of soft tissue.

Reflection of the cervical vertebra, for example, which is superimposed over the shadow of the front tooth portion and is inevitable in a dental panoramic apparatus, can be mitigated to some extent by performing weighting for emphasizing the count data of a higher-energy range when reconfiguring the front tooth portion. The similar weighting process can be used for mitigating the superimposition of the side tooth rows, or for mitigating reflection of opposite-side jaws in performing, so-called, orthogonal imaging. Further, in the case where one desires to have a closer look at the mandibular canal or the like with good contrast, he/she can perform the weighting for emphasizing the count data of a lower-energy range in performing reconfiguration to thereby achieve clearer imaging.

In the present embodiment, the semiconductor cells S and the data acquisition circuits $51n$ corresponding to the respective N acquisition pixels Sn are integrally configured using CMOSs in an ASIC. As a matter of course, the data acquisition circuits $51n$ may be configured as a circuit or a device separate from the group of semiconductor cells S.

Figure 6:
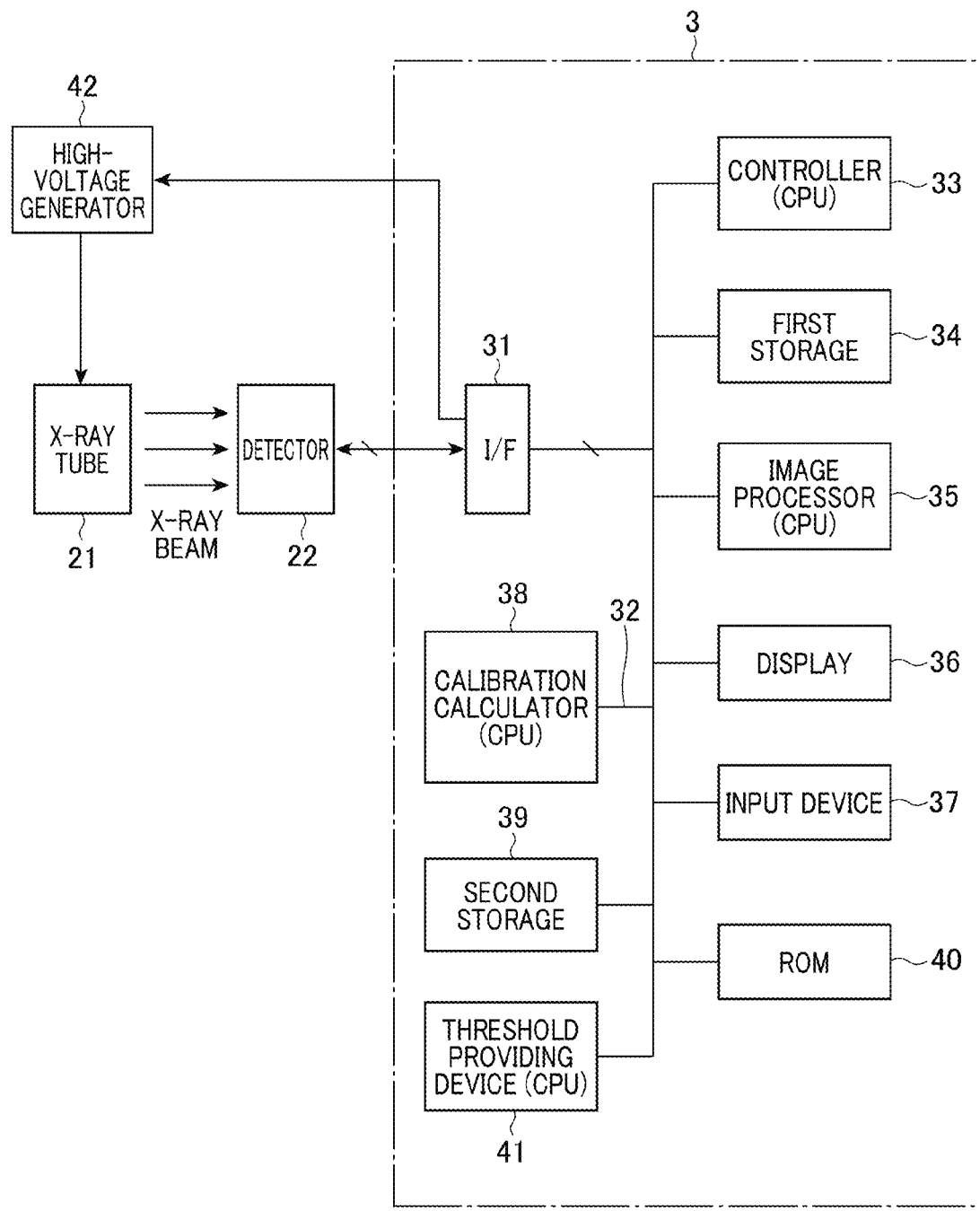
FIG. 6 is a block diagram schematically illustrating an electrical configuration of the panoramic imaging apparatus.

As shown in FIG. 6, the console 3 includes the interface (I/F) 31 that plays a role of inputting/outputting signals. The console 3 also includes the controller 33, first storage 34, image processor 35, display 36, input device 37, calibration calculator 38, second storage 39, ROM 40 and threshold providing unit 41, which are connected to the interface 31 via a bus 32.

The controller 33 controls the activation of the gantry 2 along a program given in advance to the ROM 40. The control also includes transmitting a command value to a high-voltage generator 42 that supplies high voltage to the X-ray tube 21, and giving an activation instruction to the calibration calculator 38. The first storage 34 stores frame data transmitted from the gantry 2 via the interface 31.

Under the control of the controller 33, the image processor 35 processes the frame data stored in the first storage 34 using the tonnosynthesis method based on a known calculation method called shift and add, in accordance with the program given in advance to the ROM 40. The image processor 35 then prepares an X-ray transmission image (tomographic image) of a tooth row in an oral portion of the object being examined P. The display 36 plays a role of displaying the prepared transmission image, or displaying the information showing the operating conditions of the gantry 2 and the operating information of an operator provided via the input device 37. The input unit 37 is used for an operator to give information necessary for imaging to the system.

Under the control of the controller 33, the calibration calculator 38 operates in accordance with the program incorporated in advance in the ROM 40, and calibrates digital thresholds for distinguishing energy, the thresholds being provided to each energy discrimination circuit of each acquisition pixel Sn in a data acquisition circuit described later. The calibration may be performed in a factory before shipment of the panoramic imaging apparatus, or may be performed in a periodic maintenance or the maintenance in the occurrence of failure, or may be performed before performing imaging. The calibration forms the main features of the present invention and will be specifically described later. The second storage 39 memorizes the values of the thresholds prepared for each acquisition pixel and for each energy discrimination circuit.

The thresholds are called up under the control of the controller 33 in performing imaging, provided to the data acquisition circuit described later and subjected to calibration.

Under the control of the controller 33, the threshold providing unit 41 calls up the digital thresholds stored in the second storage 39 in performing imaging, for each acquisition pixel and for each discrimination circuit to transmit the thresholds as command values to the detector 22 via the interface 31. In order to perform this processing, the threshold providing unit 41 executes the program stored in advance in the ROM 40.

The controller 33, the image processor 35, the calibration calculator 38 and the threshold providing unit 41 all include a CPU (central processing unit) that operates in accordance with given programs. The programs are stored in advance in the ROM 40.

(Calibration)

Hereinafter are described the significance, conditions and specific method, and the like, of the calibration in the present embodiment.

In the detector 22 shown in FIG. 3, all the acquisition channels CNn are manufactured with CMOSs. The acquisition channels CNn extend from the semiconductor cells S to the serial converters 59 to output the count data of all pixels. Accordingly, for the first reason that there may be a manufacturing error, or the like, it will be inevitable that the detection characteristics are varied in all the acquisition channels CNn. Therefore, this has to be corrected by calibration. In addition, the detector 22 is a photon counting type device. Therefore, the D/A converters $57_i$ (i=1 to 4) have to be provided for each acquisition channel, the D/A converters $57_i$ having a plurality of discrimination circuits (system number i=1 to 4) for discriminating the energy of the X-ray photons and converting digital command values (thresholds) to analog values for each discrimination circuit (second reason). For the first and second reasons, the detection characteristics are varied between the acquisition channels (i.e. between discrimination circuits in terms of the same threshold, in the plurality of acquisition channels CNn).

Figure 7:
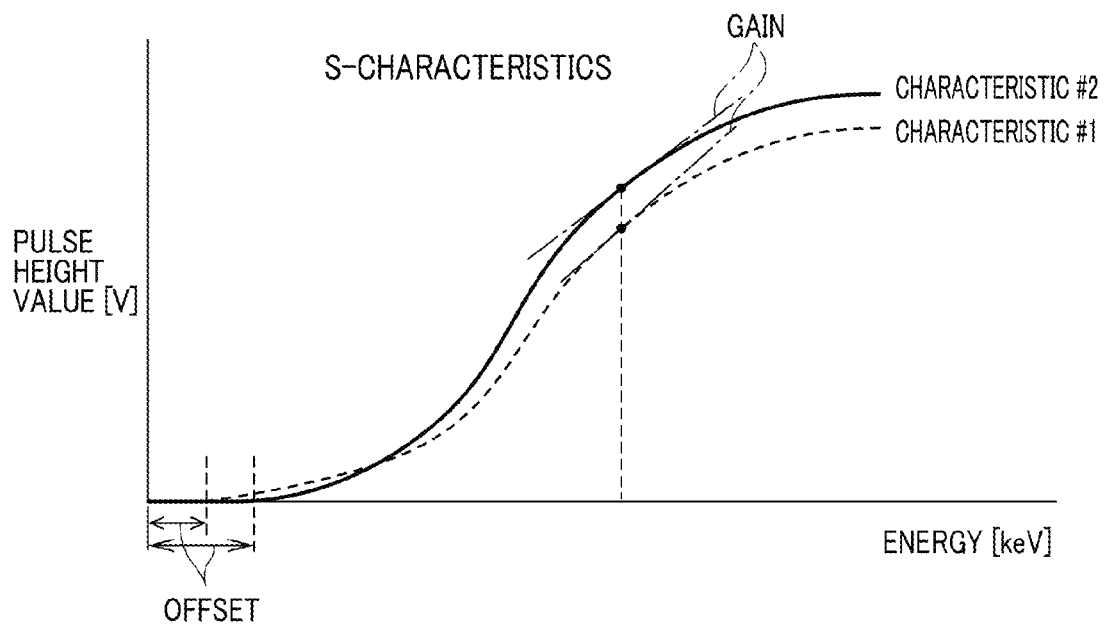
FIG. 7 is a graph illustrating variation of S-characteristics of the detector.

Regarding the first reason, let us refer to the graph shown in FIG. 7. The graph shows a relationship between the height of a pulse signal detected upon incidence of X-ray photons and the energy value of the photons in each acquisition channel. Generally, as shown in FIG. 7, the relationship is expressed by an S-shaped curve. This is a non-linear graph which is normally called S-characteristics. The offset and the gain of the S-characteristics, and the curved shape itself of the shape of S are different between the acquisition channels (e.g., an acquisition channel 1 has characteristics #1 and the adjacent acquisition channel has characteristics #2). This is inevitable however fine manufacture may be performed from the viewpoint of hardware. Such a variation causes difference in detection sensitivity and naturally leads to impairing detection capability. Therefore, calibration is required to be performed to eliminate or suppress such a variation and to retain high detection sensitivity.

As described above, calibration for uniforming the S-characteristics has conventionally been performed. The calibration makes use of two types of gamma-ray sealed radiation sources, such as $^{241}$Am (energy value is 59.5 keV) and $^{122}$Co (energy value is 122 keV), having known fixed energy values to acquire data, and adjust the thresholds for discriminating energy on the basis of the results of the acquisition, so that the offset and the gain are uniformed between the acquisition channels. However, in using the two types of gamma-ray sources, the S-characteristics are merely uniformed at two points thereof (positions corresponding to the energy values of 59.5 keV and 122 keV) and accordingly the adjustments at the points other than at these points are unknown. Therefore, in the conventional calibration method, reliability of the set thresholds is quite low with respect to the energy values at the points other than at these two points. Further, it takes a long time (e.g. several to several tens of hours) for acquiring a sufficient amount of data from all of the pixels using the gamma-ray sources. Accordingly, work efficiency is quite low and not practical.

Figure 8:
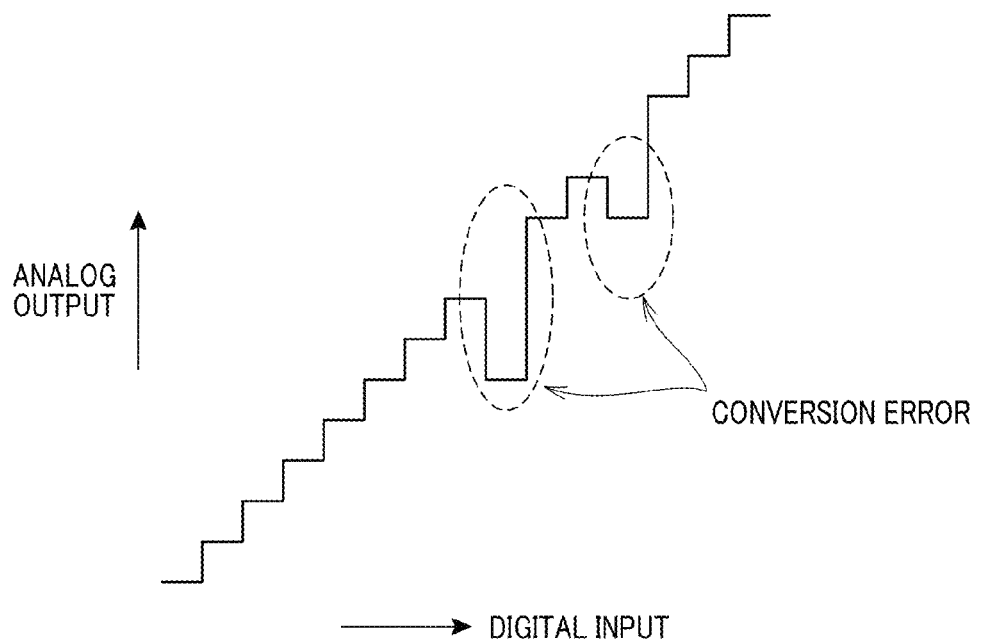
FIG. 8 is a graph illustrating conversion error that may be caused by a D/A converter.

Regarding the second reason, let us refer to FIG. 8 showing D/A characteristics of the D/A converter $57_t$ (t=1 to 4). As shown in FIG. 8, a conversion error (in the case of monotonous variation with the rate of change being different between steps, or in the case of non-monotonous variation) may be caused. Energy discrimination is essential in the photon counting type detector 21. If finer energy discrimination is desired to be performed, a more number of D/A converters is required to be set per pixel, i.e. per acquisition channel. Therefore, it has been necessary to perform calibration, taking account of the conversion error shown in FIG. 7. However, sufficient measures have not been taken for the conversion error.

In this regard, the greatest characteristic of the present panoramic imaging apparatus is that the apparatus has a function of performing calibration, eliminating these inconveniences.

This calibration is ensured not to be performed by using a plurality of types of radiation sources, such as a gamma-ray source and an X-ray source, but performed by using only an X-ray source in as shortest a time as possible with high accuracy. In the present embodiment, the X-ray tube 21 is used as this X-ray source.

Measurement conditions under which calibration of the present embodiment is performed will be described. In the present embodiment, calibration is performed in a state where various conditions are set so that count loss of the detector 22 is reduces as much as possible. These conditions are referred to as optimum measurement conditions. The optimum measurement conditions of the present embodiment are composed of two conditions, both of which are set in order to reduce count loss. Of the two optimum measurement conditions described below, only one of them may be used depending on the conditions of implementation. This may also be effective in reducing count loss.

The first optimum measurement condition indicates performing calibration with energy which is set such that the actual count will be even between individual energy ranges as much as possible, when, for example, the actually used X-ray tube voltage is 80 kV. The condition includes current (tube current) supplied to the X-ray tube 21 in performing calibration. In particular, the tube current is set in a state where X-ray beams are radiated to the entire sensor surface and each acquisition pixel Sn is provided with thresholds which are lower than all desired types (values) of thresholds provided for energy discrimination. In this state, the tube current is set such that the count rate will be 1/10 of the count rate which indicates logical 1% count loss of X-ray particles (pileup phenomenon) and is in accord with the shape of an X-ray spectrum acquired in each acquisition pixel Sn and the time taken for shaping an outputted electric pulse signal. The tube current is set in accordance with the energy of X-ray beams, i.e. the voltage (tube voltage) applied to the X-ray tube 21.

Figure 11:
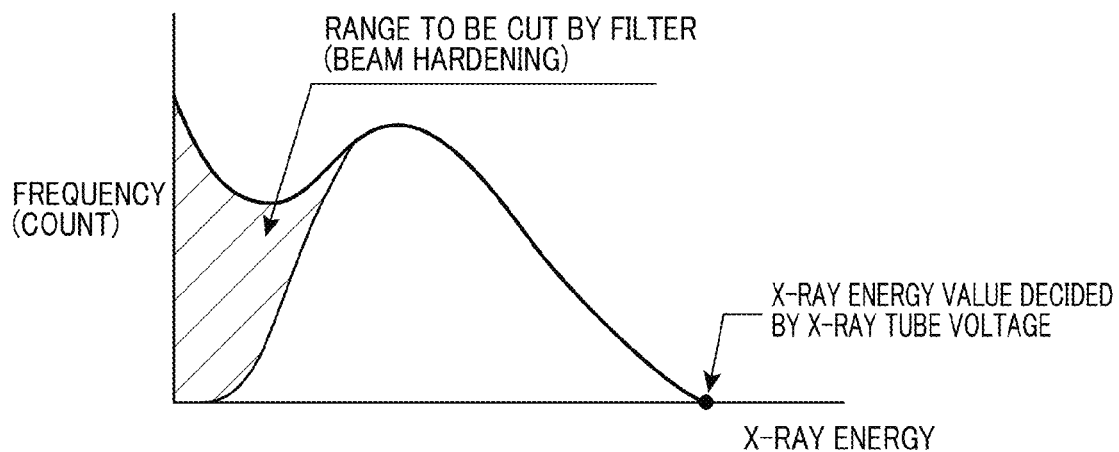
FIG. 11 is a diagram illustrating functions of a filter.

The second optimum measurement condition is to perform beam hardening of the spectrum of the X-ray beams incident on the detector 22 to harden the entire spectrum waveform (cause beam hardening). A filter FT made of a resin (see FIG. 9 described later) is placed in front of the X-ray tube 21 only when calibration is performed. The X-ray beams radiated from the X-ray tube 21 are hardened, as schematically illustrated in FIG. 11, by being permitted to pass through the filter FT. In terms of spectrum, X-ray particles having lower energy are easily superimposed (piled up) over X-ray particles having higher energy. Hardening of the X-ray spectrum will reduce the number of X-ray particles having low energy and accordingly there will also be a low probability that the X-ray particles are superimposed in an energy band desired to be calibrated. For example, the filter FT is a plate member made of acryl or aluminum with a thickness of 20 mm. The filter FT is placed at a position in front of the X-ray tube 21 by the operator's setting a support mechanism, not shown, or activating an automatic mounting mechanism, not shown, in performing calibration. Depending on a tube voltage desired to be adjusted, it is desirable that a different material is used for the filter FT. As a matter of course, the filter FT is removed at least from the X-ray radiation path when calibration is not performed.

Table 1 shows an example of measurement conditions, taking account of the first and second optimum measurement conditions, in the case where the distance between the detector 22 and the focal position of the X-ray tube is 55 cm. The information shown in Table 1 is stored in advance in the form of a memory table in the calibration calculator 38 or the second storage 39 and referred to as necessary.

TABLE 1

| X-ray energy | Tube voltage | Tube current | Type of filter | Start value of energy threshold | Acquisition width of energy threshold |
|---|---|---|---|---|---|
| Discrimination circuit 1: 30 keV | 29 kV | 1.0 mA | Acryl, 20 mm thickness | $TH_1ST = 15$ | $TH_w = 30$ |
| Discrimination circuit 2: 39.5 keV | 39 kV | 3.5 mA | Aluminum, 10 mm thickness | $TH_2ST = 20$ | $TH_w = 35$ |
| Discrimination circuit 3: 48 keV | 48 kV | 4.8 mA | Aluminum, 20 mm thickness | $TH_3ST = 25$ | $TH_w = 50$ |
| Discrimination circuit 4: 59 keV | 59 kV | 5.0 mA | Aluminum, 20 mm thickness | $TH_4ST = 45$ | $TH_w = 50$ |

In Table 1 set forth above, the filter thickness is 10 mm when the X-ray energy=39.5 keV is established, and the filter thickness is 20 mm when the X-ray energy has other values. The threshold and the threshold width are indicated with a relative value obtained when a continuous value is quantized to 1 to 128, the continuous value being of the energy in terms of a spectrum obtained when the X-ray energy is set to a possible maximum value. What is more important is that, for each discrimination circuit $DS_i$, the start value $TH_iST$ of an energy threshold and the acquisition width $TH_w$ thereof are set so as to have a minimum but sufficient range that can fully shake them up and down without fail, centering on the X-ray energy (determined by tube voltage) (see FIG. 17 described later). Since the calibration performed in the present invention is to find an energy threshold at which a Count is substantially truly 0, the above range is set so as to achieve this.

In the present embodiment, an optimum value is calculated in an X-ray acquisition period as well. The acquisition period is set in order to maintain a given level or more of statistical acquisition accuracy of calibration. In the present embodiment, the acquisition period is set to 200 frames. Calibration is ensured to be performed by adding up the frame data of the 200 frames. As a matter of course, the number of frames is not necessarily limited to 200 frames but are determined, taking account of statistical acquisition accuracy against noise, counting time and the like. Accordingly, the number of frames can be reduced by slightly changing other conditions of design or by devising ways of processing.

Hereinafter, calibration is specifically described.

As described above, the present panoramic imaging apparatus is calibrated before factory shipment or after being set up in the field, or when the detector is periodically changed or changed in the occurrence of abnormality. As a mechanism for performing calibration, the console 3 includes the calibration calculator 38, the second storage 39 and the threshold providing unit 41.

As described above, the detector 22 includes a plurality of detection modules $B_1$ to $B_N$. Therefore, two types of calibration are performed, which are a "global" calibration (hereinafter referred to as global calibration: first calibration) and a calibration called "trim" (hereinafter referred to as trim calibration: second calibration) which is performed parallel to or after the global calibration. In the global calibration, detection characteristics are firstly uniformed between the plurality of detection modules $B_1$ to $B_N$. In the trim calibration, detection characteristics are uniformed, for the energy discrimination circuits, between the plurality of acquisition pixels Sn (n=1 to N) residing in each single detection module $B_1$ (to $B_M$). Uniforming detection characteristics, here, refers to correcting thresholds (command values) for energy discrimination given to the energy discrimination circuits so as to be trimmed in each discrimination circuit, and providing the corrected thresholds to the D/A converters $57_t$ (t=1 to 4) via the latch circuit 58, for all the acquisition pixels Sn of the detector 22.

Further, the present embodiment also has a feature of detecting bad pixels (or defective pixels) among the acquisition pixels Sn, preceding the global calibration or while the global calibration is performed. The bad pixel (or defective pixel), here, refers to an acquisition pixel disabled to detect X-ray beams, or an acquisition pixel outputting an abnormal detection value, i.e. an acquisition pixel that cannot be used for X-ray imaging.

In the present first embodiment, bad pixels are ensured to be detected first and then the global calibration and the trim calibration are ensured to be parallelly performed. As a matter of course, as a modification, the global calibration may be performed in parallel with detection of bad pixels, and the trim calibration may be performed for the pixels, excepting the bad pixels.

As shown in FIG. 2, each of the plurality of acquisition pixels Sn configuring a sensor surface 22F of the detector 22 is a unit for acquiring X-ray transmission data under the measurement of X-ray particles. Therefore, each of the acquisition pixels Sn is a start point of the acquisition channel CNn described above. Also, one acquisition channel CNn is connected with one or more energy discrimination circuits which are implemented in a semiconductor layer inside the channel. In other words, each acquisition channel CN is connected with a plurality of (four here) discrimination circuits. Accordingly, calibration refers to adjusting, for each energy threshold, the digital threshold th' (calibration data) corresponding to the analog threshold th so that detection sensitivity is uniformed between the discrimination circuits, with respect to all of the acquisition channels CN.

Hereinafter are specifically described detection of bad pixels and a process of calibration. In the calculation for calibration provided below, the "command value" is set as calibration data, for each acquisition channel CNn (=1 to N) and for each discrimination circuit $DS_i$ (i=1 to 4).

Figure 9:
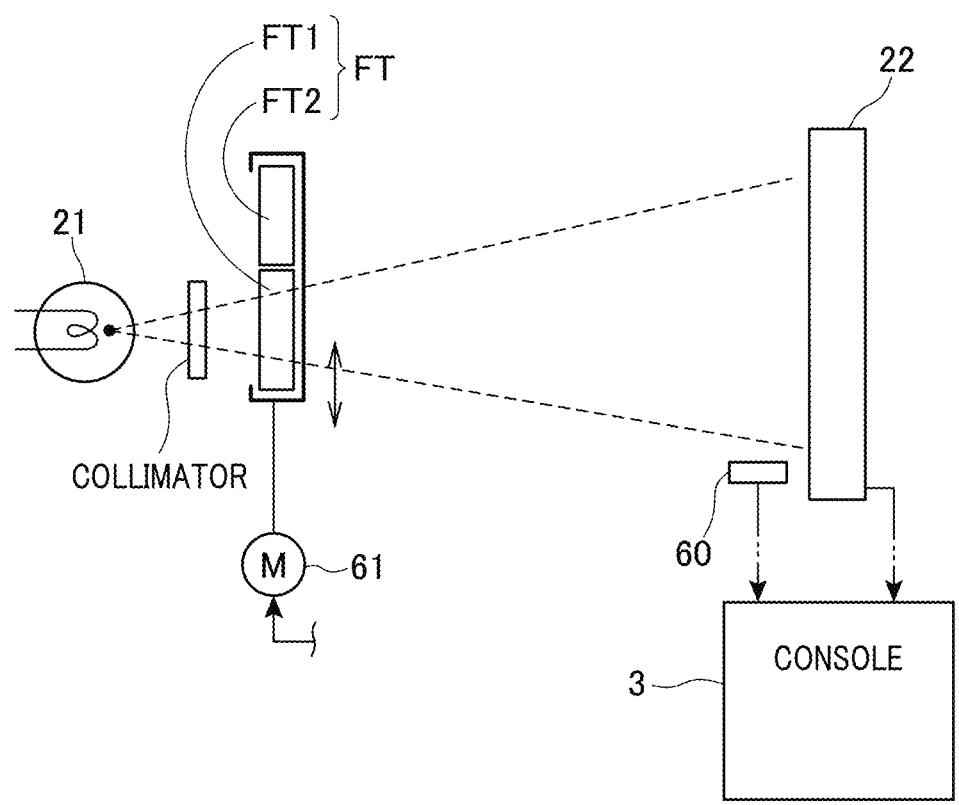
FIG. 9 is a diagram illustrating an imaging system used for calibration.

When performing detection of bad pixels and calibration, unlike normal imaging, the filter FT is inserted, as shown in FIG. 9 between the X-ray tube 21 and the detector 22. Also, a spectrum analyzer 60 is located near the detector 22. As described above, the filter FT is disposed in an X-ray path for the purpose of hardening the radiation quality of the X-ray beams (see FIG. 11). As the filter FT, one type or a plurality of types filters FT may be selectively used, in terms of the quality of material and thickness. The filter FT may be manually set every time it is needed, or may be automatically mounted using a drive mechanism 61, such as a motor. The spectrum analyzer 60 measures the actual value of energy of the X-ray beams radiated from the X-ray tube 21 and transmits the measured value to the calibration calculator 38 of the console 3. The calibration calculator 38 uses the measured value to feedback-control the X-ray tube voltage to be instructed to the high-voltage generator 42. Thus, the calibration calculator 38 is ensured to reliably allow the energy of the actually radiated X-ray beams to be set to the command value.

(Detection of Bad Pixels)

Figure 10:
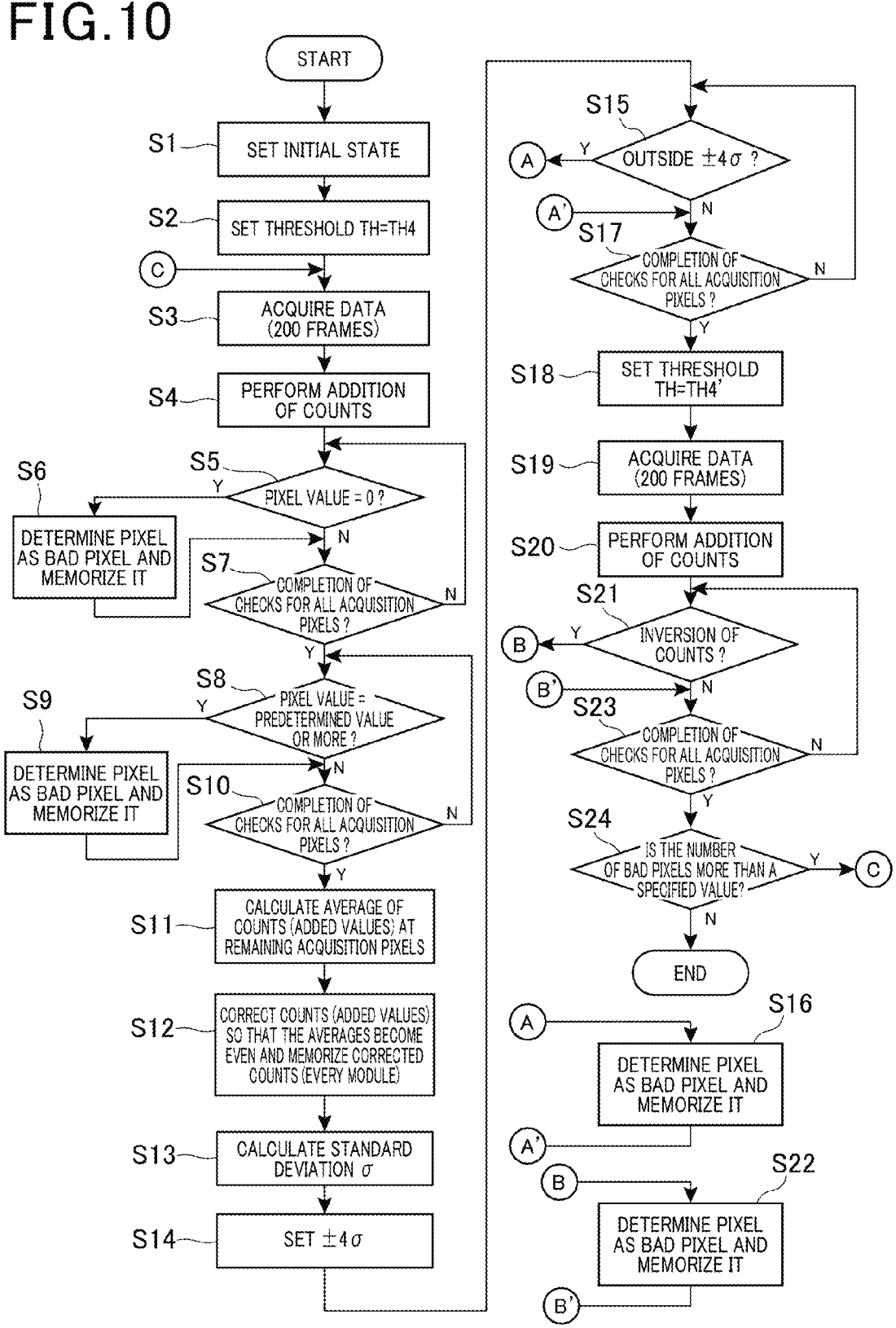
FIG. 10 is a flow diagram schematically illustrating a process of bad pixel detection.

Firstly, referring to the flow shown in FIG. 10, detection of bad pixels (bad acquisition pixels) is described. The process based on this flow is performed when the controller 33 responds to the operating information of an operator provided by the input device 37, and instructs the calibration calculator 38 to detect bad pixels.

First, the calibration calculator 38 specifies an initial state of X-ray radiation, interacting with the operator (step S1 of FIG. 10). The specification of an initial state involves specification of not only specified values of the tube voltage and the tube current of the X-ray tube 21, but also the number of acquisitions of frame data and the first placement of the filter FT (manual or automatic placement). Here, the tube voltage of the X-ray tube 21=59 kV, the tube current thereof=4 mA, the number of frames to be acquired=200 frames, and the filter FT=aluminum plate of 20 mm thick are specified (instructed).

Then, control proceeds to step S2, at which the calibration calculator 38 instructs, as an example, an identical energy threshold TH=TH4=45 (relative value) to all discrimination circuits $DS_i$ (i=1 to 4) of each acquisition pixel Sn (n=1 to N) (step S2). The processings which are going to be performed currently are collectively "detection of bad pixels". However, actually, the processings are "detection of defects in the acquisition channels CNn (n=1 to N)". Not only when the semiconductor cells C are defective, but also when any portion of one or more circuits including the discrimination circuits $DS_i$ downstream thereof have malfunction, these are, as a whole, defects of the acquisition channels. Accordingly, including detection of malfunction of all the discrimination circuits $DS_i$, bad pixels are detected on an acquisition-channel basis.

The energy threshold given to the discrimination circuits $DS_i$ does not necessarily have to be TH=TH4, but may be TH3, TH2 or TH1.

Then, at step S3, the calibration calculator 38 instructs the controller 33 to acquire frame data corresponding to 200 frames. In response to this instruction, the controller 33 transmits a drive signal to the high-voltage generator 42. The high-voltage generator 42 then drives the X-ray tube 21 with the set tube voltage. Thus, the X-ray beams radiated from the X-ray tube 21 are applied to the detector 22 via the filter FT and detected as frame data of 50×1450 pixels provided by the plurality of detection modules B1 to Bm.

The frame data are acquired by an amount corresponding to the instructed number of frames, i.e. 200 frames in the present embodiment. Each frame data acquired then is a measured value of X-ray particles having an energy value exceeding the energy threshold TH=TH4. Since an identical threshold th4 corresponding to the energy threshold TH=TH4 is applied to all of the discrimination circuits $DS_i$ (i=1 to 4) of each acquisition pixel Sn, the count acquired via each acquisition channel CNn (n=1 to N) is larger than the count acquired when one system of the discrimination circuit $DS_i$ is connected to each acquisition pixel Sn (n=1 to N), by a difference from the count of four systems. Accordingly, the difference of the count may be used as it is for detecting bad pixels, or may be averaged per one system for detecting bad pixels.

When the high-voltage generator 42 drives the X-ray tube 21, the spectrum analyzer 60 mentioned above finely adjusts the tube voltage of the X-ray tube 21 using the actually measured X-ray energy value. Thus, the energy value of the X-ray beams radiated from the X-ray tube 21 is more highly accurately retained to the value specified as a specified value at step S1.

After completing the data acquisition, control proceeds to step S4. At step S4, each pixel value of frame data, i.e. each count of photons measured by each acquisition pixel, is added up between frame data corresponding to 200 frames. Thus, frame data of 50×1450 pixels is prepared, in which each pixel value is composed of the count obtained by adding up photons.

Figure 12:
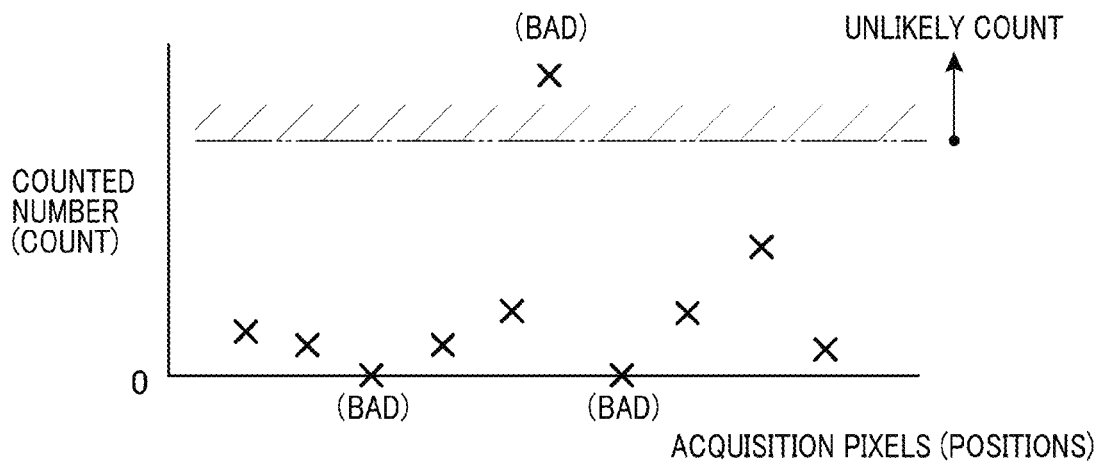
FIG. 12 is a diagram illustrating one mode of detecting bad pixels.

Further, at step S5, the calibration calculator 38 determines whether or not the count (addition value) is 0, with respect to each pixel of frame data of 50×1450 pixels. This determination is a first determination in the detection of bad pixels. As shown in FIG. 12, count (addition value)=0 means that nothing has been detected. Therefore, if the determination at step S5 is YES, control proceeds to step S6. At step S6, the pixel is determined to be a bad pixel and the address of the bad pixel is memorized.

After step S6 and if a NO determination is made at step S5, control proceeds to step S7. At step S7, each of all the acquisition pixels is determined as to whether or not it has been checked. Thus, the determination as to whether or not count (addition value)=0 is established, is separately made for each of the discrimination circuits of 50×1450 pixels (step S7). If this check has not been completed, control returns to step S5.

In the four discrimination circuits $DS_i$ (i=1 to 4) of an acquisition pixel Sn (n=1 to N), the count (addition value) acquired via one discrimination circuit may be 0, while the count (addition value) acquired via each of other three discrimination circuits may not be 0. In such as case as well, at the point when a count (addition value)=0 has firstly been found, the pixel is determined to be bad and classified into a category of bad pixel. Therefore, for the acquisition pixel already determined to be a bad pixel, even when there still remain the discrimination circuits that have not yet been determined, no further determination is made as to whether not count (addition)=0 is established. This scheme also applies to a second to fourth detections of bad pixels described later.

After completing the first detection of bad pixels, control proceeds to a second detection of bad pixels (steps S8 to S10). First, at step S8, it is determined whether or not the count (addition value) of each of acquisition pixels is equal to or more than a predetermined value that is an unlikely count. This determination is made with respect to the acquisition pixels in the frame data of 50×1450 pixels, excepting the bad pixels resulting from the determination in the first detection of bad pixels. The "predetermined value" is set to enable a determination as to what is unlikely to happen in a normal measurement of X-ray particles (see FIG. 12).

If the determination at step S8 is YES, control proceeds to step S9. At step S9, similar to step S6 described above, bad pixels are determined and memorized. Similar to the above, at step S10, it is determined whether or not check for bad pixels has been completed for each of all the acquisition pixels, excepting the bad pixels in the frame data of the 50×1450 pixels, the bad pixels resulting from the determination in the first detection of bad pixels. If this check has not yet been completed, control returns to step S8.

After completing the second detection of bad pixels, control proceeds to a processing of checking for variation of counts, i.e. a third detection of bad pixels, using a standard deviation (steps S11 to S16). First, an average value $\mu$ of counts (addition values) of each of the detection modules are calculated (step S11). The average value $\mu$ is calculated with respect to the acquisition pixels excepting the bad pixels removed as a result of up to the second detections of bad pixels.

Subsequently, for each detection module, the count of each acquisition pixel is corrected so that the average values $\mu$ of counts of the respective detection modules calculated at step S11 become even, and the corrected count is memorized (step S12). Further, a standard deviation $\sigma$ is calculated using the corrected count (step S13) and a range of ±4$\sigma$ is set on the basis of the standard deviation $\sigma$ (step S14: see FIG. 13).

Figure 13:
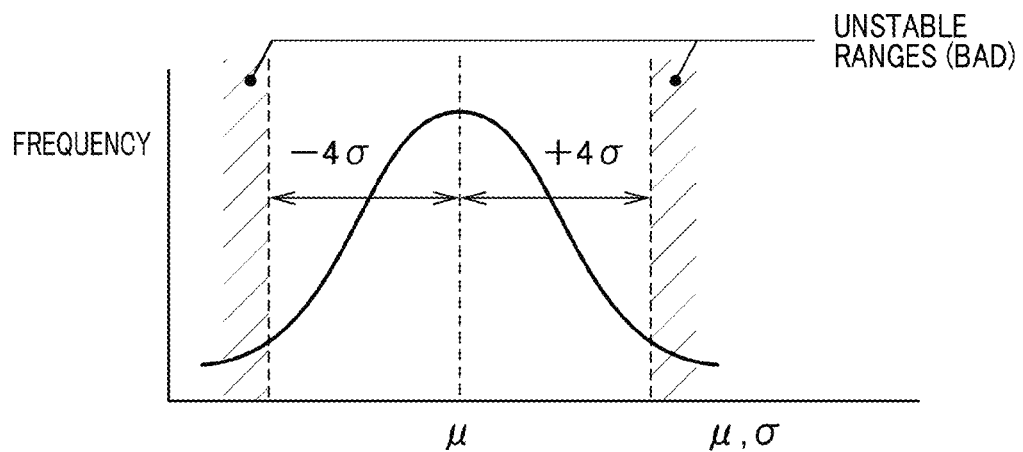
FIG. 13 is a diagram illustrating another mode of detecting bad pixels.

Then, with respect to each of the remaining acquisition pixels other than those determined to be bad pixels in up to the second detection of bad pixels, it is determined whether or not the count (addition value) calculated at step S4 for each acquisition pixel is out of the range of "average value $\mu$±4$\sigma$" (step S15: see FIG. 13). If this determination is YES, control proceeds to step S16 at which the pixel is determined to be bad and the address thereof is memorized in a similar manner described above. After this processing, or if the determination at step S16 is NO, the similar processing is repeated for the remaining acquisition pixels (step S17). Thus, the third detection of bad pixels is performed with respect to all the acquisition pixels determined to be good in the first and second detections of bad pixels.

After that, the value of the energy threshold TH is changed to detect the pixels that show statistically unlikely measured values as being bad pixels. This is a fourth detection of bad pixels which is performed in combination with the first and second detections of bad pixels, in which the confirmation is simply based on count, and the detection of bad pixels based on variation, which makes use of the standard deviation. By performing the first to fourth detections of bad pixels, the reliability of bad-pixel detection is more enhanced.

The fourth processings for bad pixels is shown in steps S19 to S23. First, an instruction is given for increasing the energy threshold TH to TH4' (e.g., TH4'=50 (relative value)> TH4=45 (relative value)) (step S19). The energy threshold TH may be instructed to be decreased from TH4=45 (relative value). Then, in a state where the energy threshold TH has merely been changed, frame data of 200 frames are acquired, similar to the above steps S3 and S4 (step S20). Further, the pixel value, i.e. the count of each acquisition pixel, is added up between the data of the 200 frames (step S21).

Figure 14:
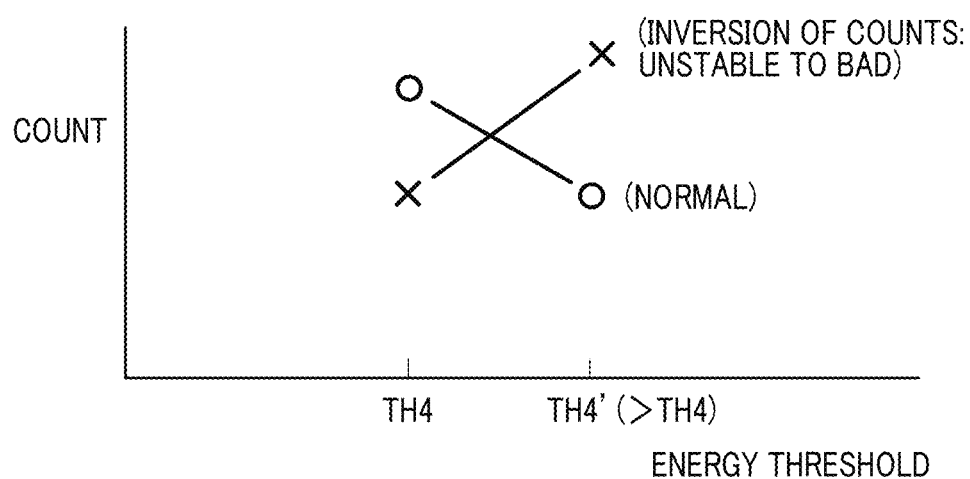
FIG. 14 is a diagram illustrating still another mode of detecting bad pixels.

When this is ready, comparison is made between a count (addition value) A at the time of the energy threshold TH=TH4 calculated at the above step S4 and a count (addition value) B at the time of the energy threshold TH=TH4' (>TH4) calculated at the above step S20. Specifically, it is determined whether or not the latter count B>A is established (i.e. whether or not the counts are inverted) for each acquisition pixel (step S21). If this determination is YES (the counts are inverted), which is statistically unlikely, the pixel is determined to be a bad pixel having instability and the address thereof is memorized (step S22). FIG. 14 shows the concept of the inversion of the counts. The determination as to whether or not these counts are inverted is sequentially and individually made for all of the remaining acquisition pixels, irrespective of the first to third detections of bad pixels (step S23). In this way, the processings for the fourth detection of bad pixels are terminated.

Finally, at step S24, it is determined whether or not the number of bad pixels (bad acquisition channels) detected through the series of processings described above is equal to or more than a specified value (e.g., 5% of the number of all pixels). If this determination is YES, i.e. if bad pixels, the number of which is equal to or more than the specified value, are still found, the calibration calculator 38 returns the process to step S3. Thus, the processings described above are repeatedly performed. In this repetition, if the determination at step S24 is NO, the number of detections of bad pixels is determined to have converged in the repetition. Then, the series of detections of bad pixels is terminated.

By the time of the termination, the information for specifying detected bad pixels, i.e. addresses, are memorized in an internal memory of the calibration calculator 38. Accordingly, in imaging, the counts acquired through the acquisition channels CNi starting from the acquisition pixels Si at the positions of these addresses are ensured not to be used, and the counts therefor are estimated by interpolation from the surrounding pixels.

The number of times of return from step S24 to step S3, i.e. the number of times of repetition of the bad-pixel detections, may be limited to a predetermined value (e.g., four times). Specifically, it may be determined that repetition of detections more than the predetermined value will not reach the conversion of the number of detections of bad pixels. Then, the process may be given up and terminated. In this case, the detector 21 in the entirety would have been caused a serious defect in manufacturing.

(Calibration)

Figure 15:
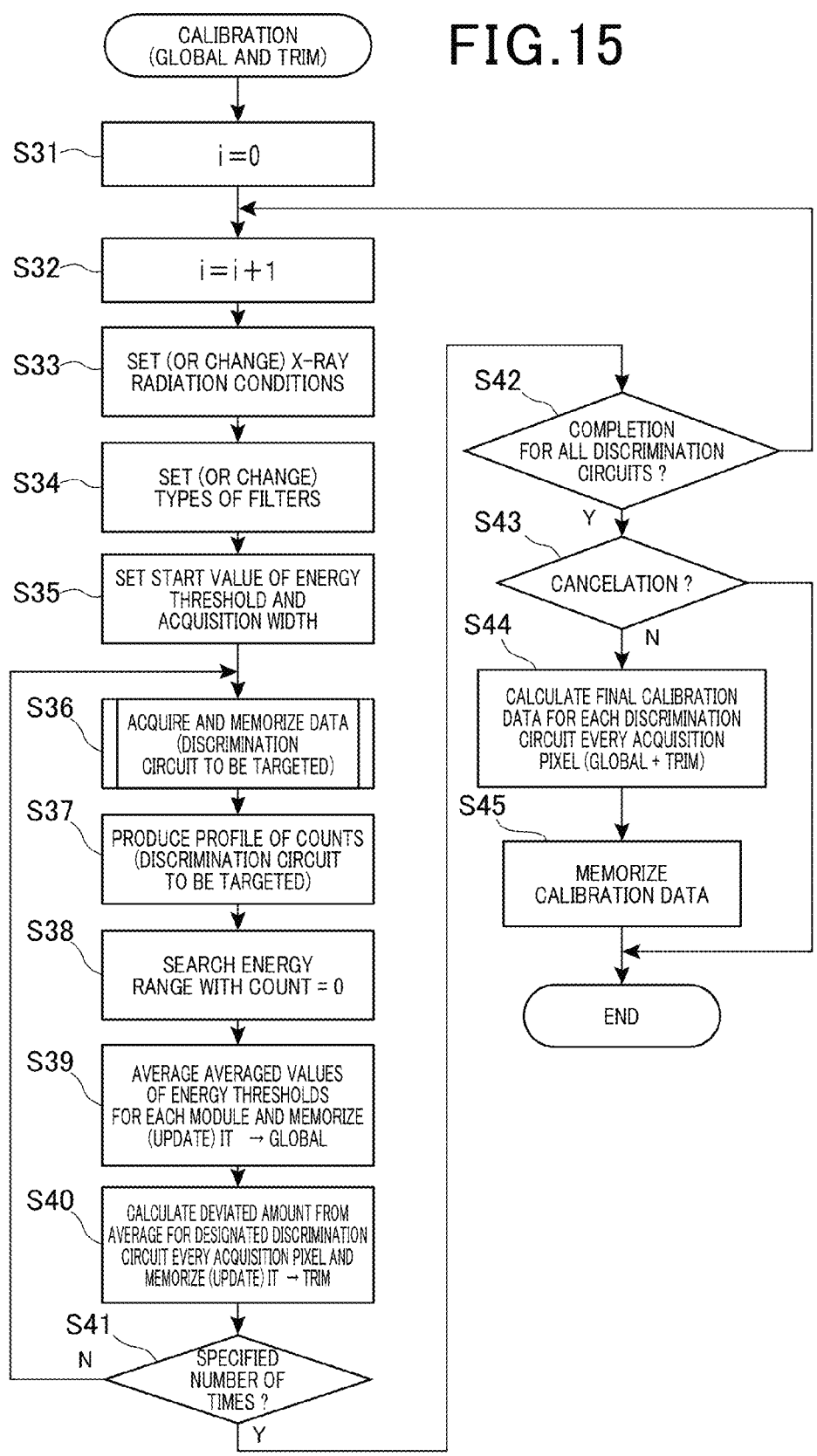
FIG. 15 is a flow diagram schematically illustrating a process of calibration.
Figure 16:
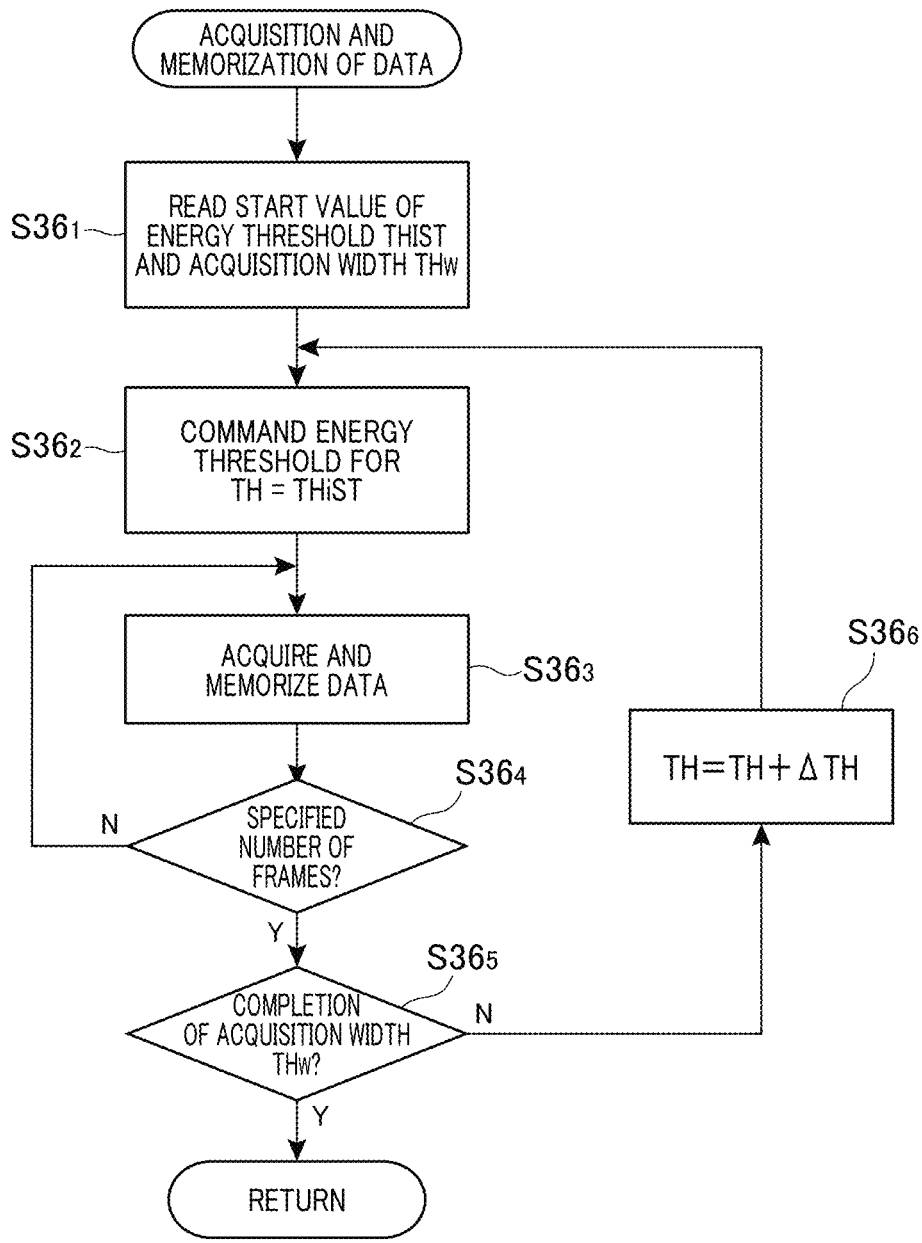
FIG. 16 is a flow diagram of a sub-routine illustrating a process of data acquisition and storage performed in a part of FIG. 15.

When the detections of bad pixels are completed as described above, the calibration calculator 38 allows the control to proceed to the global and trim calibrations. FIGS. 15 and 16 schematically show the processes for the calibrations.

As will be described later, the calibrations are ensured not to be performed for the acquisition channels which are understood to have bad pixels as a result of the pre-processing described above. Thus, calculation load for the calibrations is reduced as much as possible to increase speed.

First, at step S31, the calibration calculator 38 sets a variable i to 0, the variable i indicating the number of discrimination circuits $DS_i$ parallelly connected to each acquisition pixel Sn. Then, at step S32, variable i=i+1 is calculated. Further, control proceeds to step S33 at which X-ray radiation conditions, such as the tube current and the tube voltage of the X-ray tube 21, are set or changed. In the present case, since variable i=1 is set, a first discrimination count $DS_1$ is specified. The discrimination circuit $DS_1$ indicates a discrimination circuit that uses the D/A converter $57_1$ and the comparator $54_1$ of FIG. 3. The tube current and the tube voltage provided to the discrimination circuit $DS_1$ are determined by the system 1) in Table 1 described above. In the present case, tube voltage=29 kV and tube current=1.0 mA are set.

Subsequently, at step S34, an instruction is given for setting or changing the filter FT used for hardening the radiation quality of X-ray beams. As will be understood from Table 1, the filter FT is also determined depending on which of the discrimination circuits $DS_i$ has been specified. When the filter FT to be used is determined, the drive mechanism 61 is driven, as shown in FIG. 9, or, a filter FT1 (e.g., aluminum plate of 10 mm, 20 mm thickness) or a filter FT2 (acryl plate of 20 mm thickness) is manually placed in the X-ray path. In the present case, the filter FT2 (acryl, 20 mm thickness) is used.

Then, control proceeds to step S35 at which a start value of the energy threshold and an acquisition width are set for the currently selected discrimination circuit $DS_i=DS_1$. This setting is also performed with reference to the memory table which is stored as Table 1. For example, when discrimination circuit $DS_i=DS_1$ is established, the start value is $TH_1ST=15$ and the acquisition width is $THw=30$ (both are relative values).

When this is ready, at step S36, the calibration calculator 38 carries out data acquisition and memorization of 200 frames, for example, set in advance as a specified number of frames, with respect to the first discrimination count $DS_1$, in the similar manner based on the instruction at the time of detecting bad pixels described above. FIG. 16 shows a process of the data acquisition and memorization as a sub-routine.

Figure 17:
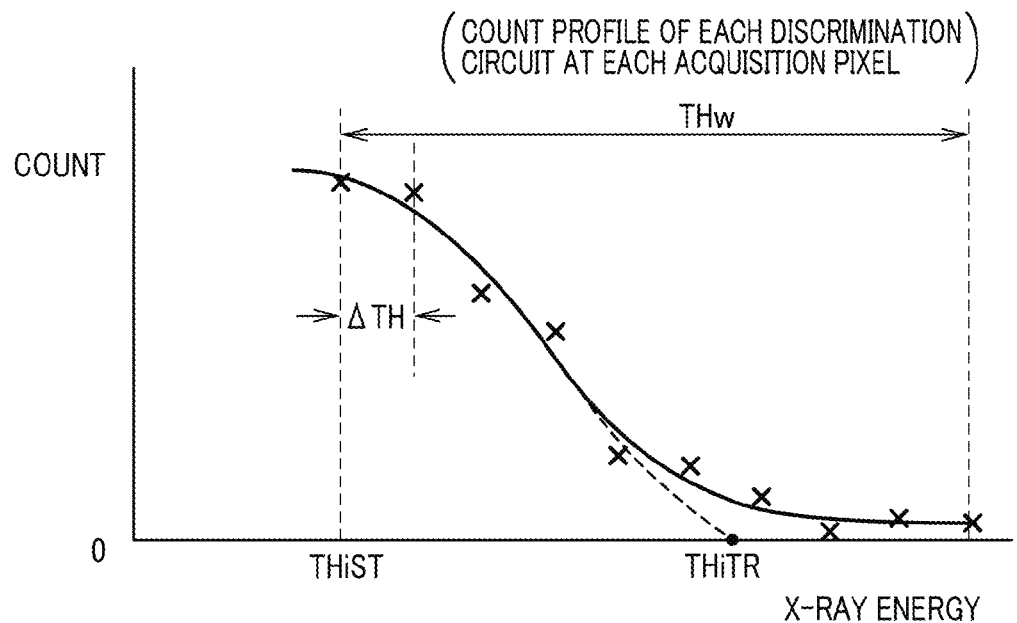
FIG. 17 is a diagram illustrating estimation of an energy threshold for a count of 0.

Specifically, as shown in FIG. 16, the set values for the energy threshold (start value $TH_1ST=15$, acquisition width $THw=30$) are read out (step $S36_1$: see FIG. 17). Further, of the set values, the start value $TH_1ST=15$ is provided, as current energy threshold TH ($TH=TH_1ST$), to the corresponding comparator $54_1$ via the latch circuit 58 and the D/A converter $57_1$ configuring the first discrimination circuit $DS_1$ (step $S36_2$). In this instance, the same start value may be provided to the remaining second to fourth discrimination circuits $DS_2$ to $DS_4$, or a different value may be provided. In any case, the data that has been acquired through the discrimination circuits having nothing to do with the discrimination circuit currently dealt with are ignored.

In this state, data (counts) are acquired and memorized for the specified number of frames (e.g., 200 frames) (step $S36_3$ and $36_4$). Then, it is determined whether or not the current energy threshold has reached the maximum value of the acquisition width, i.e. "start value $TH_1ST$+acquisition width $THw=15+30$" (step $S36_5$). If the determination is YES, the sub-routine of the acquisition and memorization is terminated and control returns to the main routine. On the other hand, if the determination is NO, calculation for $TH=TH+\Delta TH$ is performed for increment by an amount corresponding to a threshold stride $\Delta TH$ (step $S36_6$). As shown in FIG. 17, the threshold stride $\Delta TH$ is set in advance to a predetermined value, with which change of count in increasing the energy threshold can be accurately grasped. After step $S36_5$, the process returns to step $S36_2$ and is repeatedly performed until $TH=TH_1ST+THw=15+30$ is reached.

After completing the process of the sub-routine, main step S37 shown in FIG. 15 is performed again. Specifically, as shown in FIG. 17, at step S37, using the counts for the specified number of frames (e.g., 200 frames) acquired at step S36, a profile thereof is prepared. In the figure, x mark indicates a count. The count is prepared for each discrimination circuit $DS_i$ of each of the acquisition pixels and the value is an average value of the counts for 200 frames, for example.

Then, at step S38, the calibration calculator 38 applies a multidimensional function or the like to the prepared profile to perform correction and fitting. Then, as shown in FIG. 17, the calibration calculator 38 estimates the energy threshold $TH_iTR$ with which the count that decreases with the increase of the energy threshold becomes 0. In the present case, since calibration is performed for the first discrimination circuit $DS_1$ (i=1), the energy threshold $TH_iTR$ is estimated for the first discrimination circuit $DS_1$ of each acquisition pixel Sn (n=1 to N).

In practice, as shown in FIG. 17, even after exceeding the energy threshold $TH_iTR$, count does not immediately converge, but the state of gradual decrease of low count continues. This is an upward shift phenomenon of energy spectrum due to pileup of X-ray pulses. This phenomenon is suppressed by the beam hardening caused by the filter FT used in the present embodiment. However, in practice, the phenomenon cannot necessarily be entirely suppressed. Therefore, it is important to estimate the energy threshold that depends on the tube voltage and fairly truly establishes count=0, without being influenced by this phenomenon.

Figure 18:
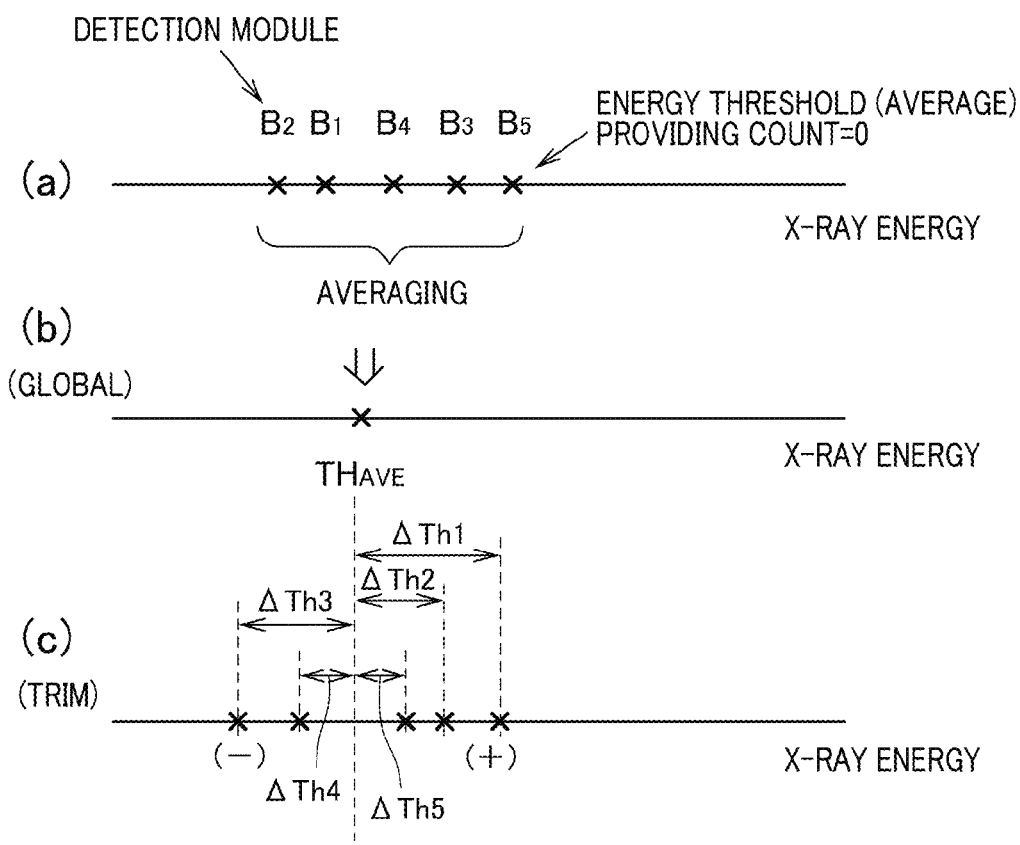
FIG. 18 is a diagram illustrating processing associated with the energy thresholds of count=0 for each detection module, and calculation of calibration with respect to each discrimination circuit of each acquisition pixel, based on the results of the processing.

After this, the calibration calculator 38 performs the global calibration and the trim calibration using the energy threshold $TH_1TR$ described above. First, at step S39, for each detection module, an average value of the energy thresholds $TH_1TR$ is calculated of the first discrimination circuit $DS_1$, and further, an average value of the energy thresholds $TH_1TR$ is calculated of the plurality of detection modules (step S39). This average value is calculated as a representative value and does not necessarily have to be an averaged value. Thus, as shown in FIG. 18 by (a) and (b), the average values of the energy thresholds $TH_1TR$ of the plurality of detection modules B1 to B5 (m=5) are further averaged to obtain a single average value $TH_{AVE}$. The average value $TH_{AVE}$, which uniforms the energy threshold between the plurality of detection modules, is memorized as global calibration data.

Subsequently, at step S40, a deviated amount $\Delta th_n$ (n=1 to N) from the average value $TH_{AVE}$ of the energy thresholds $TH_iTR$ calculated at step S38 is calculated with respect to the discrimination circuit $DS_i$ of specified order of each acquisition pixel Sn of each of the plurality of detection modules. FIG. 18 schematically illustrates by (c) the concept of the deviated amounts $\Delta th_1$ to $\Delta th_5$ in the case where the number of acquisition pixels is n=1 to 5. These deviated amounts $\Delta th_n$ are used for finely adjusting the individual difference in manufacturing between the discrimination circuits of each acquisition pixel, or the deviation elements relying on the individual characteristics thereof. The deviated amounts $\Delta th_n$ are memorized as trim calibration data.

As will be described later, when the processings of steps S39 and S40 are repeated, the average value $TH_{AVE}$ is updated with the repetition.

Then, at step S41, it is determined whether or not the processings from steps S36 to S40 have been performed for the specified number of times (e.g., four times). If this determination is NO, the processings of steps S36 to S40 are repeated until the specified number of times is met. This repetition contributes to stabilizing calibration.

When preparation of the calibration data of the specified number of times is completed (YES at step S41), the calibration calculator 38 or the second storage 39 should have stored the latest global calibration data ($TH_{AVE}$) and trim calibration data ($\Delta th_n$) which have been updated by the repetition.

Further, at step S42, it is determined whether or not similar preparation of calibration data has been completed for all of the discrimination circuits $DS_i$. In the present case, processings still remain for the second to fourth discrimination counts $DS_2$ to $DS_4$. Accordingly, the determination is NO and control returns to step S32. Thus, calibration data will now be prepared for the second discrimination circuit $DS_2$. The same applies to the third and fourth discrimination circuits.

Further, at step S43, it is determined whether or not the calibration is forcibly stopped, interacting with the operator. In the absence of the stop instruction, control proceeds to steps S44 and S45, at which final calibration data are prepared for the discrimination circuits $DS_i$ of each acquisition pixel Sn. As shown in FIG. 19, this preparation is carried out by performing addition and subtraction of "global calibration data ($TH_{AVE}$)+trim calibration data ($\Delta th_n$)" (step S44) and storing the results in the second storage, for example, for each discrimination circuit of each acquisition pixel (step S45).

In the above description, the "change of filter, change of tube current" corresponds to the radiation condition setting means for suppressing pileup probability.

(Provision of Threshold)

When calibration is completed in this way, the second storage 39 should have stored optimized digital command values as calibration data. Thus, in imaging, the threshold providing device 41 provides, as command values, digital thresholds $th_t'$ (t=1 to 4) via the latch circuit 58 and the D/A converter $57_t$. The digital thresholds $th_t'$ are highly accurately calibrated for the first to fourth thresholds TH1, TH1, TH3 and TH4, i.e. correspond to the calibration data calculated at steps S44 and S45 described above. In this way, calibrated analog thresholds $th_e$ (t=1 to 4) are provided to the comparators $54_t$ of each acquisition channel.

Figure 20:
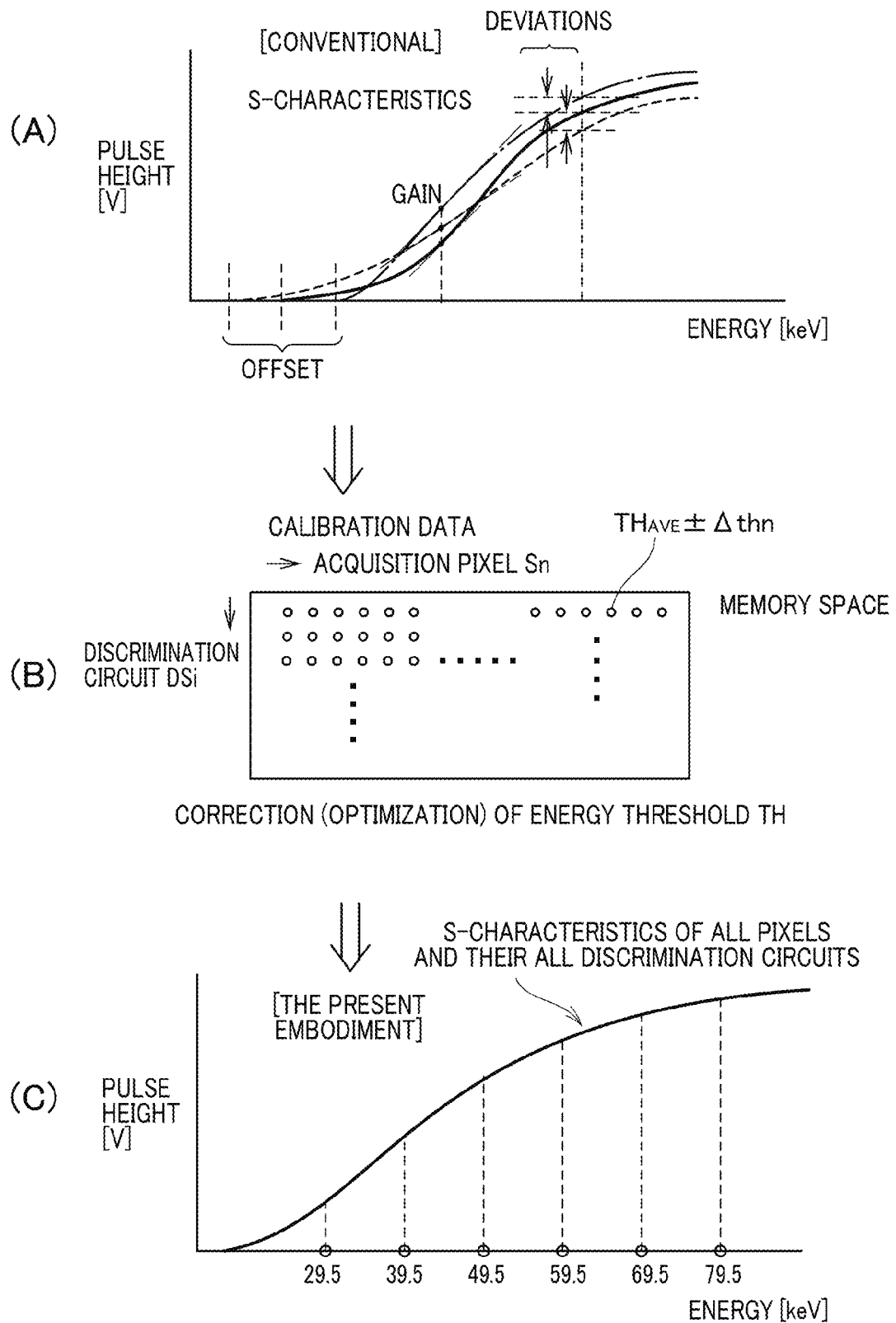
FIG. 20 is a diagram schematically illustrating the effects of calibration.

As shown in FIG. 20, S-characteristics may be different between the individual pixels or the individual discrimination circuits due to the individual difference in hardware (individual difference in the offset, gain (inclination) and peak value) (see (A) of FIG. 20). Even in such a situation, the calibration data are obtained from the optimization processings (see (B) of FIG. 20), and uniform or substantially uniform threshold characteristics for energy, at the appearance (in operational performance), can be obtained (see (C) of FIG. 20). In this way, variation in the detection sensitivity is reliably suppressed between the pixels or between the discrimination circuits, thereby obtaining high energy setting ability.

Calibration related to the present embodiment is performed as described so far. Accordingly, excellent advantageous effects that could not have been obtained conventionally can be obtained as follows.

In the first place, calibration can be performed using only the X-ray tube 21 that is one type of radiation source. Specifically, compared to the case where only gamma-ray beams are used, or where gamma-ray beams and X-ray beams are used as reference sources, calibration can be performed remarkably faster and with higher accuracy. Accordingly, the work of the operator is mitigated. This is because, for each energy threshold, the X-ray tube voltage is set focusing on only the energy desired to be set, and accordingly a threshold can be correctly set on the basis of only the tube voltage.

In the second place, in performing data acquisition for calibration, a filter for hardening radiation quality is loaded on the front surface of the X-ray tube, and the tube current and the data acquisition period are set so that the probability of pileup will be lowered. Therefore, the low-energy components of the X-ray beams can be reduced, and hence the superimposition phenomenon can be minimized, in which these components are superimposed over the energy components approximate to the tube voltage. Accordingly, the accuracy is enhanced in the calculation for processing a count.

In the third place, the global calibration is performed first as rough calibration, and using the results thereof, the fine trim calibration is performed. Thus, the detection sensitivity of all the acquisition pixels of the detector 21 can be easily converged within a predetermined range in a short time. In other words, compared to the method of directly trimming the detection sensitivity of each of the acquisition pixels, the time taken for calibration can be dramatically shortened.

In the fourth place, although the process is a calibration process, the process can detect bad pixels in advance. Moreover, the bad pixels are detected from various viewpoints, such as that measurement is completely disabled, the count is abnormal (abnormally high, abnormally scattered or unstable), or the like. Thus, reliability in the detection of bad pixels is extremely high, and the detector 22 having bad pixels will not be used as it is for imaging. Specifically, since the positions of bad pixels are memorized, the counts of the bad pixels are not used in performing image reconfiguration in imaging, but are interpolated accordingly such as from the surrounding pixels. Thus, evenness in the reconstructed image is enhanced to thereby obtain a reliable image.

In the fifth place, the bad pixels are detected preceding the calibration (the global calibration and the trim calibration). Thus, the bad pixels should have been detected by the time of performing the calibration and accordingly no calibration has to be performed for the bad pixels. In this way, the calculation load in the trim calibration is reduced and accordingly the processing speed is enhanced.

In the sixth place, the number of frames in performing measurement of counts (data acquisition) is selected to be 200 frames in order to suppress statistical noises. Thus, the accuracy in the measurement of counts is also enhanced and accordingly calibration can be performed with high reliability.

Second Embodiment

Hereinafter is described a panoramic imaging apparatus as a radiation imaging apparatus related to a second embodiment of the present invention. In describing the present embodiment, the components having functions identical with or similar to those of the first embodiment are given the same reference numerals for the sake of omitting or simplifying explanation.

The panoramic imaging apparatus related to the second embodiment is different from the apparatus of the first embodiment in the method of calculating the global and trim calibration data. Accordingly, the calibration calculator 38 performs the process shown in a partial flow diagram of FIG. 21. The rest of the configuration and process is similar to the first embodiment.

Figure 21:
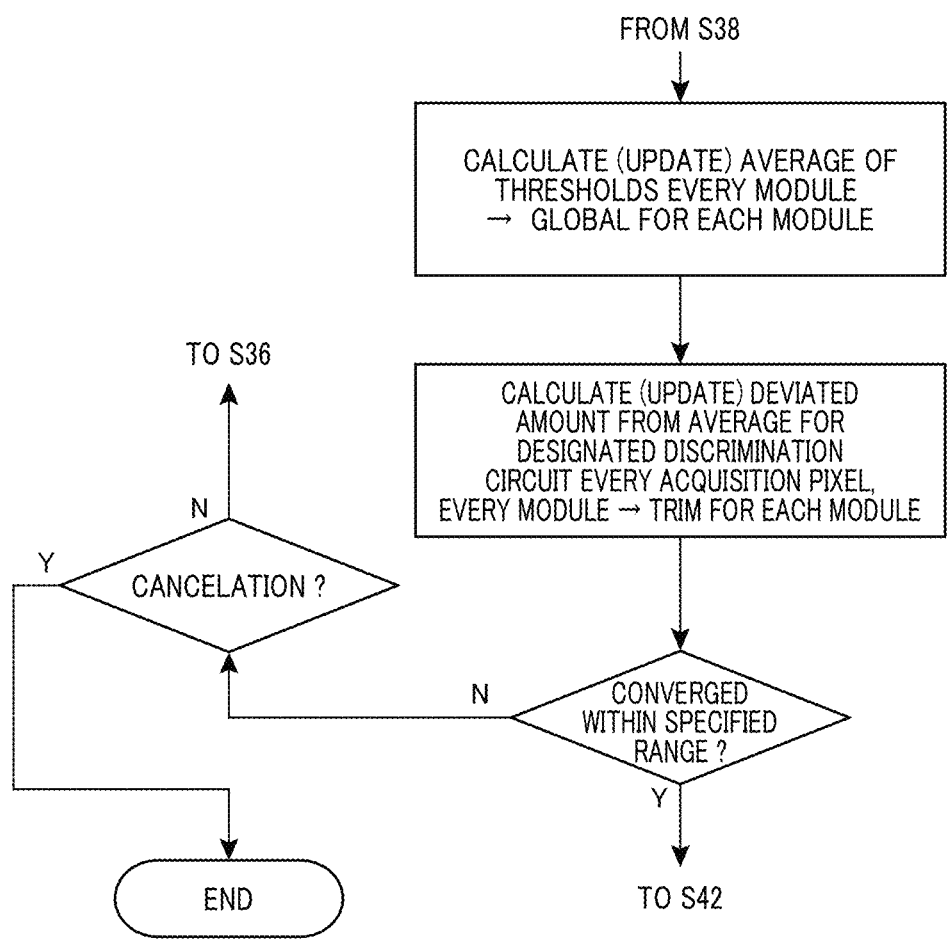
FIG. 21 is a partial flow diagram illustrating a process of calibration performed in a dental panoramic imaging device as a radiation imaging apparatus, according to a second embodiment of the present invention.

As shown in FIG. 21, following step S38, the calibration calculator 38 proceeds to step S39'. At step S39', the calibration calculator 38 calculates an average value $TH_{AVE-m}$ of the energy thresholds $TH_tTR$ in each of the plurality of modules Bm, and sets the average value $TH_{AVE-m}$ of these as global calibration data of each detection module Bm. Further, at step S40', deviated amounts (differences) $\Delta th_{N/m}$ are calculated for each detection module Bm, from the average value $TH_{AVE-m}$ of each of the acquisition pixels to set the deviated amounts $\Delta th_{N/m}$ as trim calibration data. In addition, at step S40', the processing is repeatedly performed until the global calibration data $TH_{AVE-m}$ of each detection module Bm converges within a predetermined energy range $TH_A$. The operator is ensured to give an instruction for stopping calibration in this repetition (step S46).

Figure 22:
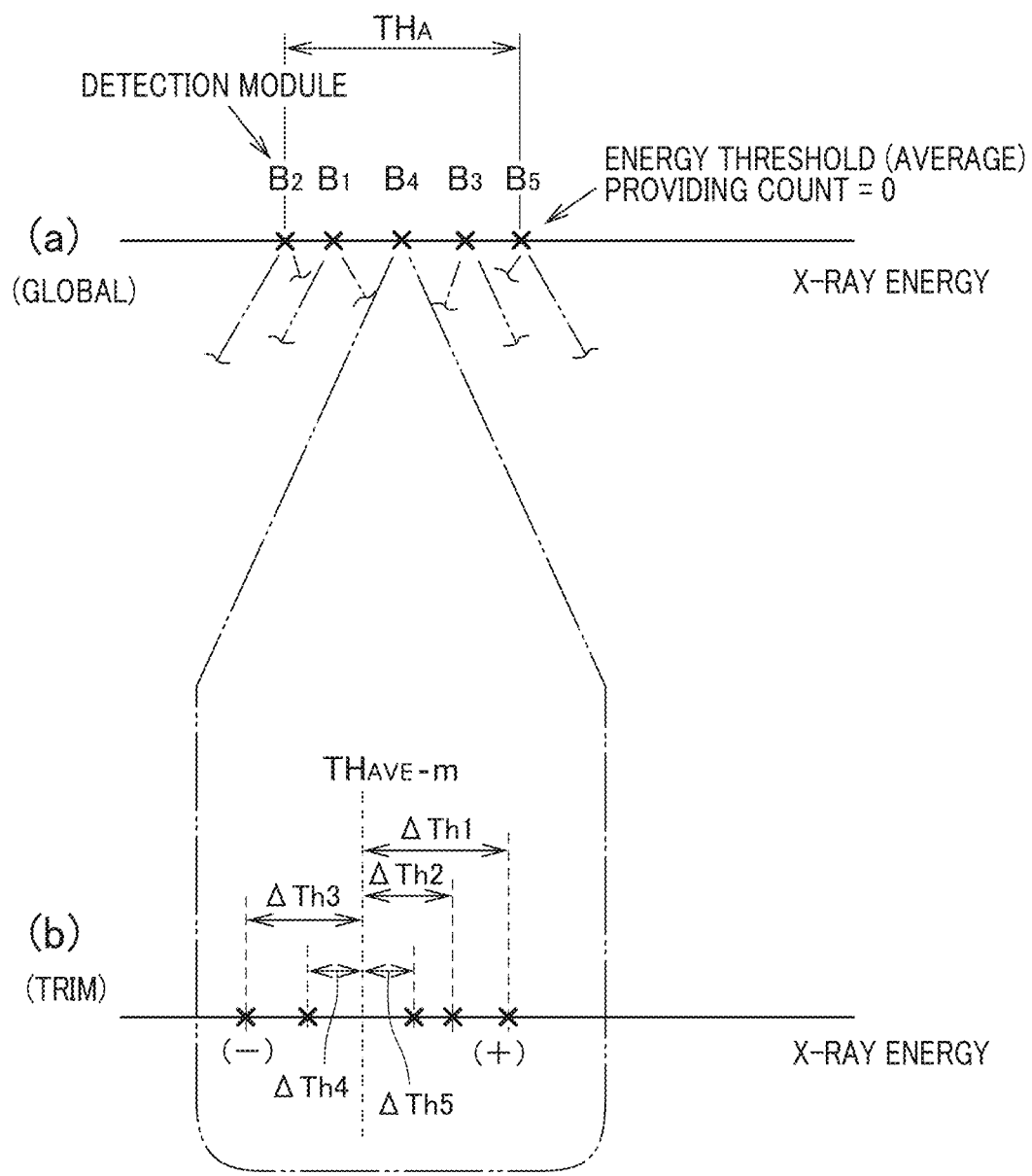
FIG. 22 is a diagram illustrating calculation of calibration data according to the second embodiment.

As a result, as shown in FIG. 22 by (a) and (b), the global and trim calibrations can be separately performed for each of the plurality of detection modules Bm. Specifically, the calibration data can be retained for each detection module Bm. Since the global calibration data has been converged within the predetermined energy range $TH_A$, the detection sensitivity of the individual acquisition pixels Sn (n=1 to N) also falls within the predetermined range when the detector is concerned as a whole. Accordingly, highly reliable calibration can still be performed. In addition, the detection modules that do not converge within the predetermined energy value range $TH_A$ are removed and those detection modules which will converge accordingly can be newly mounted. Thus, the detection modules can be dealt with on a detection-module basis. In this way, the detection modules Bm can be economically used.

The calibration method related to the foregoing first and second embodiments can be applied to various X-ray diagnostic apparatuses which are each equipped with the photon counting type radiation detector. Specifically, these embodiments may be applied not only to the dental X-ray panoramic imaging apparatus described above, but to an X-ray CT scanner for medical use or non-destructive testing, an X-ray mammography apparatus, an X-ray tonnosynthesis scanner for orthopedic use or lung cancer screening, and the like.

The invention described above is not limited to the foregoing embodiments but may be appropriately modified within a scope not departing from the spirit of the present invention. For example, in the foregoing first and second embodiments, a plurality of modularized area sensors are two-dimensionally arrayed to configure a detector. In contrast, the calibration method described above may be implemented in a line detector having a long and thin pixel area in which, in the two vertical and horizontal directions, one or more (plurality of) pixels are arranged along one direction, while a plurality of pixels are arranged along the other direction. When the plurality of pixels of the line detector are divided into a plurality of modules, the present invention can be applied thereto. When a plurality of line detectors are discretely arranged to configure a detector, each line detector can be regarded to be one module. Accordingly, similar calibration method can be performed in such a detector. Also, a planar X-ray detector for medical use or non-destructive testing, which is called flat panel, is configured by a plurality of modules. Accordingly, similar calibration method can be performed in this detector.

INDUSTRIAL APPLICABILITY

The present invention can provide a calibration method for a photon counting type radiation detector, the method being able to accurately perform calibration for each pixel in a short time. The method can exert extremely significant usability for a photon counting type radiation detector.

EXPLANATION OR REFERENCES

1 Dental panoramic imaging apparatus (radiation imaging apparatus)
2 Gantry
3 Console
12 Vertical-movement arm unit
13D Rotary shaft
12 X-ray tube (radiation source)
22 Detector
33 Controller
38 Calibration calculator
39 Second storage
41 Threshold providing device
51 Data acquisition circuit
54 Comparator
55 Energy-range distribution circuit
56 Counter
57 D/A converter
58 Latch circuit
59 Serial converter
C Semiconductor cell (pixel)
Sn Acquisition pixel
DSi Discrimination circuit
CNn Acquisition channel
FT Filter

What is claimed is:

1. A calibration apparatus used in a photon counting type of radiation detector, the radiation detector comprising:
a detector provided with a plurality of detection modules, each of the detection modules having a plurality of detection elements provided as a plurality of pixels, each of the detection elements detecting, as a photon, a radiation radiated from a radiation source and outputting an electric pulse signal whose quantity depends on energy of the photon;
at least one discrimination circuit provided for discriminating amounts of the energy in an energy spectrum of the radiation, wherein at least one energy threshold for setting a plurality of energy ranges are provided to each of the pixels;
a data production circuit producing counting data indicative of a number of particles of the radiation of every pixel and of every energy range, based on a count of the pulse signal outputted from each of the plurality of detection elements; and
an image production unit producing an image of an object based on the counting data produced by the data production circuit, when the radiation is radiated to the object, the calibration apparatus comprising:
a radiation condition setting unit setting a radiation condition of the radiation such that, when the particles of the radiations are incident on the plurality of detection modules, a probability of pileups of the incident particles is smaller than or equal to a predetermined value;
a first calibrating unit calibrating the detection modules such that, in a state where the radiation condition is set for the radiation by the radiation condition setting unit, detection sensitivities for the radiation are uniformed among the plurality of detection modules or at the respective detection modules; and
a second calibrating unit calibrating the modules, based on results calibrated by the first calibrating unit, such that the detection sensitivities for the radiation are uniform for every channel and every discrimination circuit in each channel is provided in a circuit group including, at least, the plurality of detection modules, the discrimination circuit, and the data production circuit.

2. The calibration apparatus of claim 1, wherein
the radiation source is an X-ray tube that radiates an X-ray as the radiation, and
the radiation condition setting unit includes means for setting current to the X-ray tube such that the current enables the X-ray reaching each of the pixels to have a counting characteristic which is equal to or lower than $\frac{1}{10}$ of a logical event probability, 1% at which the pulse signal piles up as a pileup phenomenon, the event probability depending on a pulse shaping time for the X-ray.

3. The calibration apparatus of claim 2, wherein
the first calibrating unit comprises,
a selecting unit selecting one of the plurality of energy thresholds for each of the plurality of pixels provided by the plurality of detection modules;
a first signal acquiring unit counting the pulse signal outputted from each of the pixels every time a voltage is applied to the radiation source, wherein the one of the plurality of the energy thresholds is selected by the selecting unit, a further threshold different from the selected one energy threshold is designated as a start value, and the voltage corresponds to an energy threshold changed by being incremented or decremented every determined value from the start value to a predetermined maximum value or a predetermined minimum value;
a zero-point estimating unit estimating an energy threshold that produces a count of zero of the pulse signal on an energy spectrum of the pulse signal obtained at each of the pixels, based on the count of the pulse signal acquired by the first signal acquiring unit;
a first calculating unit calculating, as first calibration data, a representative value of calibration for each of the plurality of modules or a representative value of calibration of the plurality of modules, based on the energy threshold estimated by the zero-point estimating unit; and
a performance repeating unit repeatedly performing the count of the pulse signal by the first signal acquiring unit, the estimation of the energy threshold by the zero-point estimating unit, and the calculation of the first calibration data by the first calculating unit at remaining ones of the energy thresholds at each of the pixels.

4. The calibration apparatus of claim 3, wherein
the second calibrating unit comprises,
a second calculating unit calculating a deviated amount of the count of the pulse signal counted by the first signal acquiring unit, from the first calibration data calculated by the first calculating unit for every one of the discrimination circuits for the respective pixels; and
a third calculating unit calculating calibration data to make uniform the detection sensitivities for the radiation by mutually adding the results calculated by both the first and second calculating units.

5. The calibration apparatus of claim 3, comprising a bad pixel detecting unit detecting, as a bad pixel, a state in which any of the pixels of the plurality of modules and the respective acquisition channel to the pixel are unsuited to counting the pulse signal.

6. The calibration apparatus of claim 5, wherein
the bad pixel detecting unit comprises
a second signal acquiring unit acquiring, for every one of the detection modules, a predetermined number of frames of the pulse signal outputted from the pixels of each of the plurality of detection modules, by allowing the radiation source to radiate the radiation to the detection modules;
a first adding unit mutually adding, pixel by pixel, among corresponding ones of the detection modules, the pulse signals of the predetermined number of frames acquired by the second signal acquiring unit; and
a first bad-pixel determining unit determining whether or not there is the bad pixel showing an abnormal behavior in added values of the pulse signal at the respective pixels of each of the plurality of modules, the added value being added by the first adding unit.

7. The calibration apparatus of claim 6, wherein
the abnormal behavior determined by the first bad-pixel determining unit is defined as a state in which the added value of the pulse signal is either zero or a statistically rare value which is equal to or more than a predetermined threshold.

8. The calibration apparatus of claim 6, wherein the bad-pixel detecting unit comprises
a histogram setting unit setting a histogram of the counts of the pulse signals from the remaining pixels, which have been acquired by the first signal acquiring unit;
a standard deviation calculating unit calculating a standard deviation based on the histogram;
a count determining unit determining, for each of the remaining pixels, whether or not there, in the counts, is a count which deviates from a range defined by multiplying the standard deviation by n wherein n is an integer of four or more; and
a second bad-pixel determining unit determining that a pixel of which count is determined by the count determining unit as being deviated from the range is a bad pixel.

9. The calibration apparatus of claim 8, wherein the bad-pixel detecting unit comprises
a third signal acquiring unit again acquiring, for every one of the detection modules, a predetermined number of frames of the pulse signal outputted from the pixels of each of the plurality of detection modules, by allowing the radiation source to radiate the radiation to the detection modules;
a second adding unit mutually adding, pixel by pixel, among corresponding ones of the detection modules, the pulse signals of the predetermined number of frames acquired by the third signal acquiring unit;
a largeness determining unit determining, at each of the pixels of each of the plurality of detection modules, whether or not there is a largeness inversion between a count mutually added by the second adding unit and a count mutually added by the first adding unit, wherein the largeness inversion is defined by a state where the count added by the second adding unit is larger than the count added by the first adding unit; and
a third bad-pixel determining unit determining that there is an abnormal pixel showing the largeness inversion determined by the largeness determining unit, the abnormal pixel being classified as the bad pixel unsuitable for imaging.

10. The calibration apparatus of claim 9, wherein
the apparatus comprises an energy measuring unit measuring an amount of energy of X-ray beams actually radiated from the X-ray tube; and
the first, second and third signal acquiring unit comprise a correcting unit correcting an amount of a high voltage applied to the X-ray tube, depending on the amount measured by the energy measuring unit.

11. The calibration apparatus of claim 1, wherein
the radiation source is an X-ray tube that radiates an X-ray as the radiation, and
the radiation condition setting unit includes means for setting current supplied to the X-ray tube such that the current enables the X-ray reaching each of the pixels to have a counting characteristic which is equal to or lower than $1/10$ of a logical event probability, 1% at which the pulse signal piles up as a pileup phenomenon, the event probability depending on both a shape of an energy spectrum of the X-ray and a pulse shaping time for the X-ray.

12. The calibration apparatus of claim 1, wherein
the at least one energy threshold is composed of a plurality of energy thresholds,
the radiation source is an X-ray tube that radiates an X-ray as the radiation, and
the radiation condition setting unit includes means for disposing a filter in front of the X-ray tube, the filter hardening radiation quality of the X-ray depending on the plurality of energy thresholds.

13. The calibration apparatus of claim 12, wherein
the filter has a thickness and a material which are set such that the filter presents a desired radiation quality depending on largeness of the energy thresholds.

14. The calibration apparatus of claim 13, wherein
the filter is composed of either an acrylic plate member of a desired thickness, which is used when the energy thresholds are lower, or an aluminum plate member of a desired thickness, which is used when the energy thresholds are higher.

15. The calibration apparatus of claim 14, wherein
the first calibrating unit comprises,
a selecting unit selecting one of the plurality of energy thresholds for each of the plurality of pixels provided by the plurality of detection modules;
a first signal acquiring unit counting the pulse signal outputted from each of the pixels every time a voltage is applied to the radiation source, wherein the one of the plurality of energy thresholds is selected by the selecting unit, a further threshold different from the selected one energy threshold is designated as a start value, and the voltage corresponds to an energy threshold changed by being incremented or decremented every determined value from the start value to a predetermined maximum value or a predetermined minimum value;
a zero-point estimating unit estimating an energy threshold that produces a count of zero of the pulse signal on an energy spectrum of the pulse signal obtained at each of the pixels, based on the count of the pulse signal acquired by the first signal acquiring unit;
a first calculating unit calculating, as first calibration data, a representative value of calibration for each of the plurality of modules or a representative value of calibration of the plurality of modules, based on the energy threshold estimated by the zero-point estimating unit; and
a performance repeating unit repeatedly performing the count of the pulse signal by the first signal acquiring unit, the estimation of the energy threshold by the zero-point estimating unit, and the calculation of the first calibration data by the first calculating unit at remaining ones of the energy thresholds at each of the pixels.

16. The calibration apparatus of claim 15, wherein
the second calibrating unit comprises,
a second calculating unit calculating a deviated amount of the count of the pulse signal counted by the first signal acquiring unit, from the first calibration data calculated by the first calculating unit for every one of the discrimination circuits for the respective pixels; and
a third calculating unit calculating calibration data to uniform the detection sensitivities for the radiation by mutually adding the results calculated by both the first and second calculating unit.

17. The calibration apparatus of claim 15, comprising a bad pixel detecting unit detecting, as a bad pixel, a state in which any of the pixels of the plurality of modules and the respective acquisition channel to the pixel are unsuited to counting the pulse signal.

18. The calibration apparatus of claim 1, wherein each of the plurality of detection elements has a pixel size equal to or less than 250 μm×250 μm.

19. The calibration apparatus of claim 1, wherein the at least one energy threshold comprises a plurality of energy thresholds which are set discretely from each other to the energy and changeable arbitrarily.

20. The calibration apparatus of claim 19, wherein the plurality of energy thresholds is given such that one or more objects are assumed as a reference and the counts for the reference measured in each of the energy ranges for a predetermined period are approximately constant, each of the counts being counted responsively to the electric pulse signal.

* * * * *